United States Patent
Buytaert

(10) Patent No.: US 12,296,174 B2
(45) Date of Patent: May 13, 2025

(54) VESTIBULAR STIMULATION CONTROL

(71) Applicant: Cochlear Limited, Macquarie University (AU)

(72) Inventor: Kristof I. Buytaert, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 426 days.

(21) Appl. No.: 17/636,675

(22) PCT Filed: Aug. 12, 2020

(86) PCT No.: PCT/IB2020/057593
§ 371 (c)(1),
(2) Date: Feb. 18, 2022

(87) PCT Pub. No.: WO2021/038355
PCT Pub. Date: Mar. 4, 2021

(65) Prior Publication Data
US 2022/0273952 A1    Sep. 1, 2022

Related U.S. Application Data

(60) Provisional application No. 62/891,499, filed on Aug. 26, 2019.

(51) Int. Cl.
*A61N 1/36* (2006.01)
*A61N 1/05* (2006.01)

(52) U.S. Cl.
CPC ....... *A61N 1/36139* (2013.01); *A61N 1/0551* (2013.01); *A61N 1/3606* (2013.01)

(58) Field of Classification Search
CPC ............ A61N 1/36139; A61N 1/36036; A61N 1/36067
See application file for complete search history.

(56) References Cited

U.S. PATENT DOCUMENTS 6,748,275 B2 *   6/2004   Lattner .............. A61N 1/36036
                                                        600/26
7,225,028 B2     5/2007   Della Santina et al.
                              (Continued)

OTHER PUBLICATIONS

International Search Report and Written Opinion in counterpart International Application No. PCT/US2020/057593, mailed Nov. 13, 2020, 9 pages.
Lee, M. Y. et al., "The Principle and Methodology of Vestibular Evoked Myogenic Potential", Research in Vestibular Science, Mar. 2015, vol. 14, No. 1, pp. 9-14.
Park, Hong Ju et al., "Frequency-tuning characteristics of cervical and ocular vestibular evoked myogenic potentials Induced by air-conducted tone burst", doi:10.1016/j.clinph.2009.10.003, Clinical Neurophysiology 121 (2010) 85-89.
(Continued)

*Primary Examiner* — George R Evanisko
(74) *Attorney, Agent, or Firm* — Edell, Shapiro & Finnan, LLC

(57) ABSTRACT

A vestibular stimulation system comprises a vestibular nerve stimulator that is configured to deliver electrical stimulation signals to the vestibular system of a recipient. The vestibular stimulation system includes a vestibular evoked myogenic potential sensing arrangement that is configured to record, over a period of time following delivery of electrical stimulation signals to the recipient's vestibular system, muscle responses potentially representative of one or more vestibular evoked myogenic potentials. The recorded muscle responses are then used to control operation of the vestibular nerve stimulator (e.g., used to set one or more parameters of the electrical stimulation signals).

23 Claims, 12 Drawing Sheets

(56) References Cited

U.S. PATENT DOCUMENTS

| | | | |
|---|---|---|---|
| 8,012,189 B1 | 9/2011 | Webb et al. | |
| 8,843,217 B1 | 9/2014 | Keller et al. | |
| 9,089,692 B2 | 7/2015 | Risi et al. | |
| 9,339,649 B2 * | 5/2016 | Cushing | A61N 1/36038 |
| 2002/0010497 A1 | 1/2002 | Merfeld et al. | |
| 2008/0300519 A1 | 12/2008 | Helt, III et al. | |
| 2010/0222695 A1 | 9/2010 | Torfs et al. | |
| 2010/0312145 A1 | 12/2010 | Ernst et al. | |
| 2012/0226187 A1 | 9/2012 | Bierer et al. | |
| 2012/0277835 A1 | 11/2012 | Della Santina et al. | |
| 2013/0066424 A1 * | 3/2013 | Hessler | A61N 1/36036 623/10 |
| 2014/0336449 A1 * | 11/2014 | Wackym | A61B 5/0051 600/25 |
| 2015/0032186 A1 | 1/2015 | Cushing et al. | |
| 2019/0021642 A1 * | 1/2019 | Rabbitt | A61B 5/163 |

OTHER PUBLICATIONS

Rosengren, S.M. et al., "Vestibular evoked myogenic potentials: Past, present and future", doi:10.1016/j.clinph.2009.10.016, Clinical Neurophysiology 121 (2010) 636-651.

Fife, Terry D. et al., "Practice guideline: Cervical and ocular vestibular evokedmyogenic potential testing", DOI 10.1212/WNL.0000000000004690, Neurology published online Nov. 1, 2017.

Van de Berg, Raymond et al., " The Vestibular Implant: Hearing Preservation during Intralabyrinthine Electrode Insertion—A Case Report", doi: 10.3389/fneur.2017.00137, Apr. 10, 2017.

Ramos de Miguel, Angel et al., "Vestibular Response to Electrical Stimulation of the Otolith Organs. Implications in the Development of a Vestibular Implant for the Improvement of the Sensation of Gravitoinertial Accelerations," J Int Adv Otol Aug. 2017; 13(2): 154-61, DOI: 10.5152/iao.2017.4216, 8 pages.

* cited by examiner

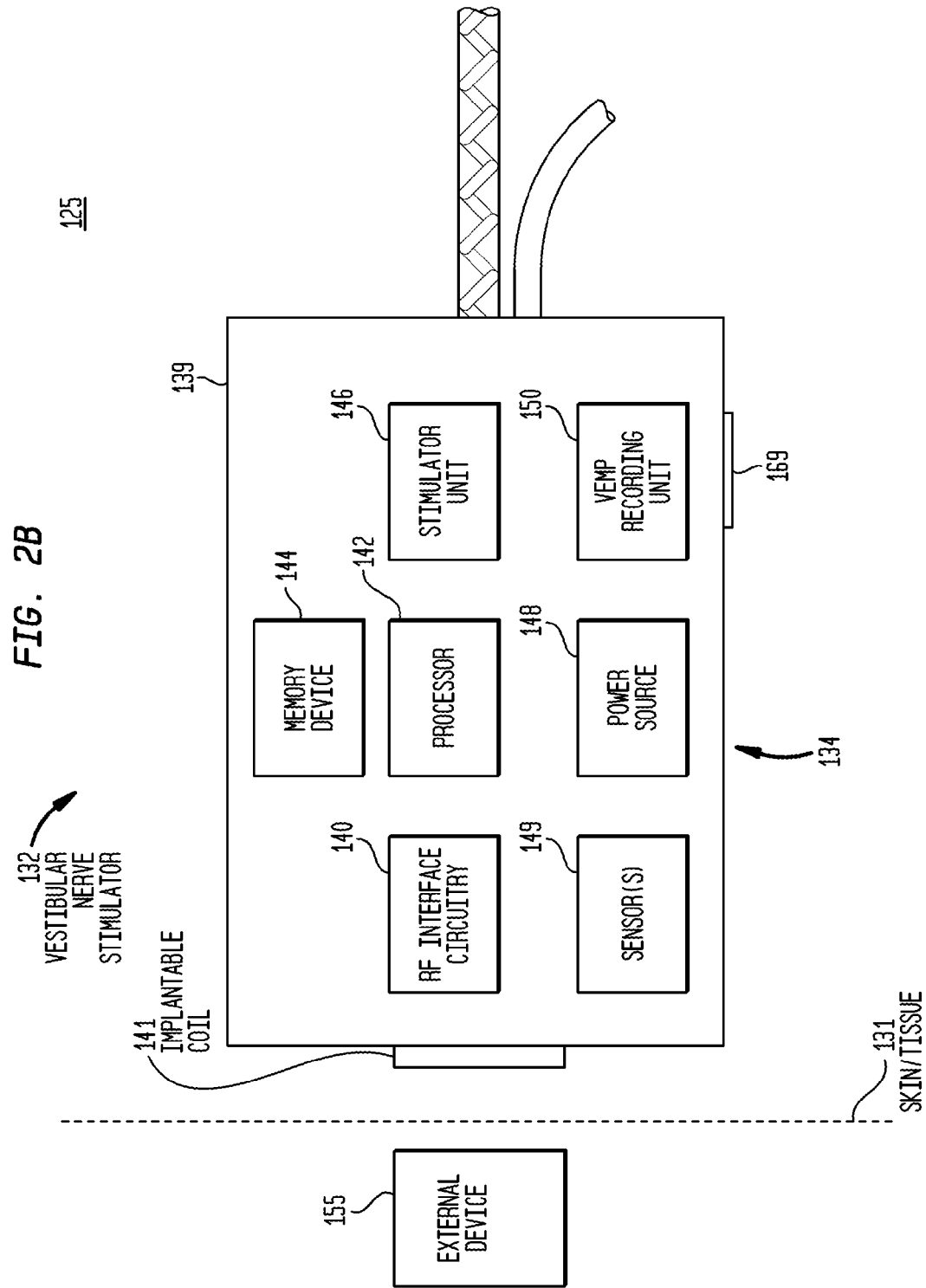

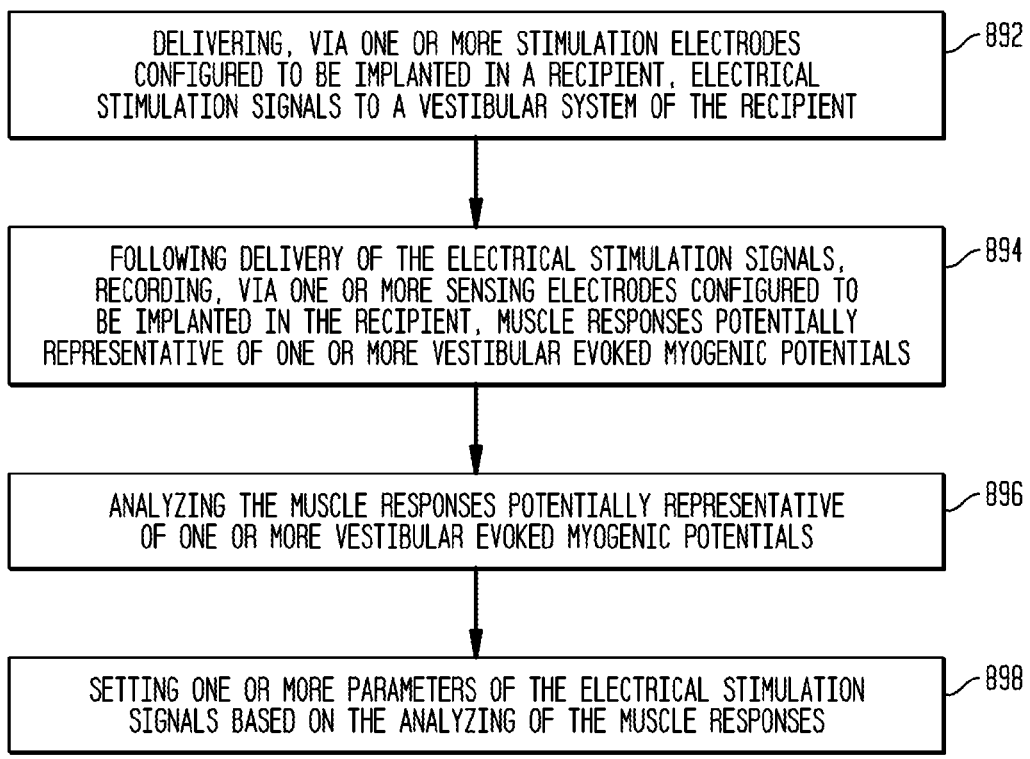

VESTIBULAR STIMULATION CONTROL

BACKGROUND

Field of the Invention

The present invention generally relates to stimulation of a recipient's vestibular system.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions and/or recipient monitoring for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In one aspect, a method is provided. The method comprises: delivering, via one or more stimulation electrodes configured to be implanted in a recipient, electrical stimulation signals to a vestibular system of the recipient; following delivery of the electrical stimulation signals, recording, via one or more sense electrodes configured to be implanted in the recipient, muscle responses potentially representative of one or more vestibular evoked myogenic potentials; analyzing the muscle responses potentially representative of one or more vestibular evoked myogenic potentials; and setting one or more parameters of the electrical stimulation signals based on the analyzing of the muscle responses.

In another aspect, a vestibular stimulation system is provided. The vestibular stimulation system comprises: a stimulating assembly comprising a plurality of electrodes configured to be implanted in an inner ear of a recipient adjacent to otolith organs of the inner ear; a stimulator unit configured to generate and deliver electrical stimulation signals to at least one of the otolith organs via one or more of the plurality of electrodes; a vestibular evoked myogenic potential sensing arrangement configured to record, over a period of time following delivery of electrical stimulation signals to the at least one of the otolith organs, responses from one or more muscles of the recipient that are associated with vestibular evoked myogenic potentials; and one or more processors configured to set at least one parameter of the electrical stimulation signals based on the responses recorded from the one or more muscles of the recipient.

BRIEF DESCRIPTION OF THE DRAWINGS

Embodiments of the present invention are described herein in conjunction with the accompanying drawings, in which:

FIG. 2B is a simplified block diagram of the vestibular stimulation system of FIG. 2A, in accordance with certain embodiments presented herein;

FIG. 8 is a flowchart of a method, in accordance with certain embodiments presented herein.

DETAILED DESCRIPTION

Presented herein are techniques for controlling operation of a balance prosthesis based on muscle responses associated with vestibular evoked myogenic potentials. In particular, a vestibular stimulation system comprises a balance prosthesis, such as a vestibular nerve stimulator, that is configured to deliver electrical stimulation signals to the vestibular system of a recipient. The vestibular stimulation system also includes a vestibular evoked myogenic potential sensing arrangement that is configured to record, over a period of time following delivery of electrical stimulation signals to the recipient's vestibular system, muscle responses potentially representative of one or more vestibular evoked myogenic potentials. The recorded muscle responses are then used to control operation of the balance prosthesis (e.g., used to set one or more parameters of the electrical stimulation signals).

Figure 1A:
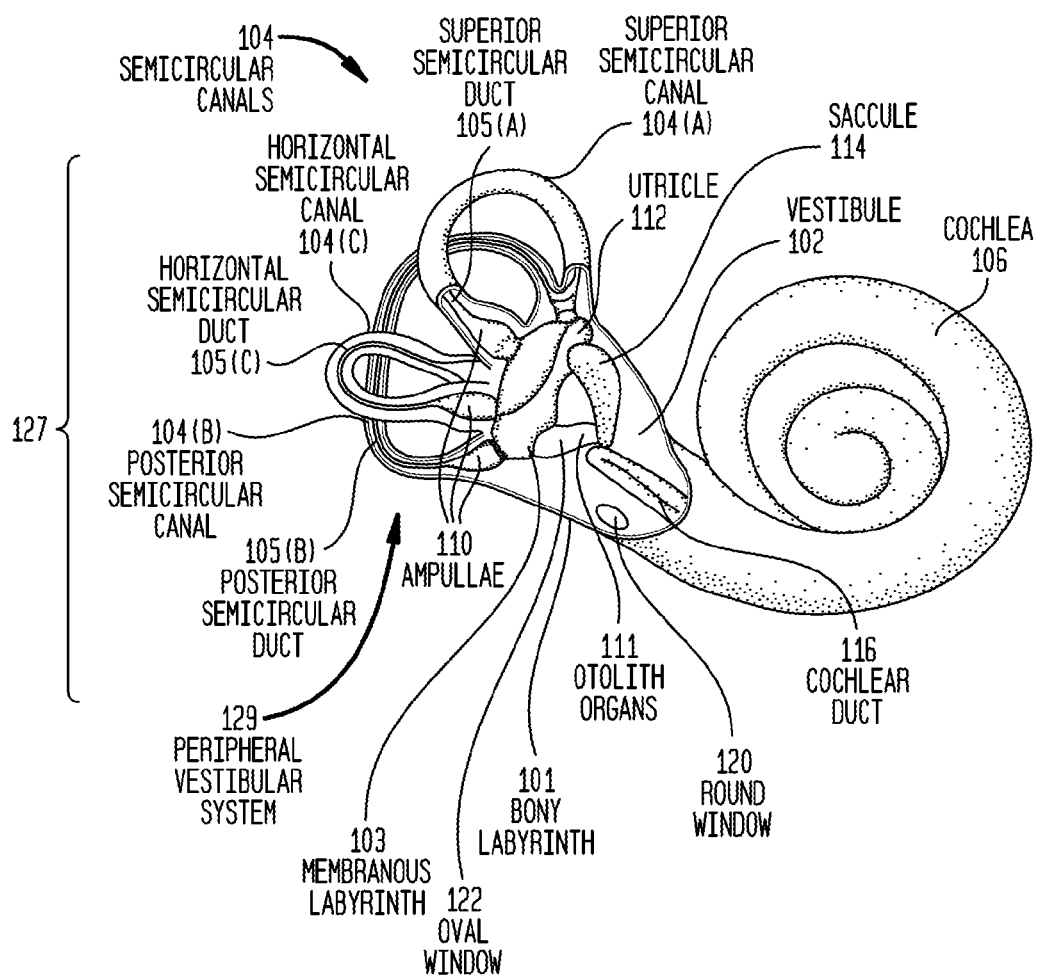
FIG. 1A is a schematic, partial cross-sectional view illustrating anatomical structures of the human inner ear.
Figure 1B:
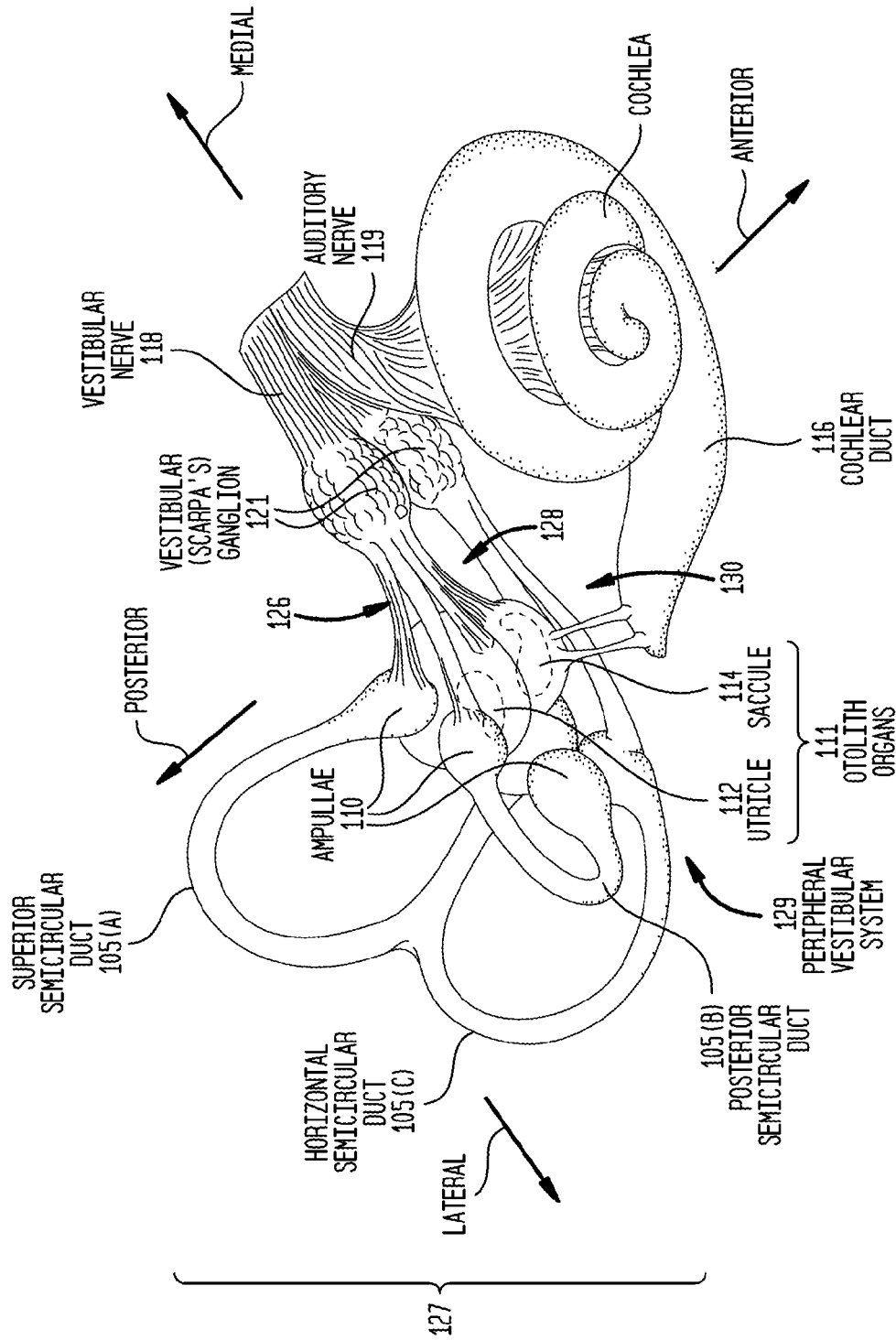
FIG. 1B is a perspective view illustrating further details of a portion of the human inner ear of FIG. 1A.

Before describing details of the vestibular stimulation control techniques presented herein, relevant aspects of an example human inner ear are first described below with reference to FIGS. 1A and 1B. In particular, shown in FIG. 1A is the bony labyrinth 101, which is the bony outer wall of an inner ear 100. The bony labyrinth 101 includes three sections/parts, referred to as the vestibule 102, which includes the otolith organs 111, the semicircular canals 104, and the cochlea 106. The vestibule 102, the semicircular canals 104, and the cochlea 106 are cavities that are internally lined with periosteum and that contain a fluid known as perilymph. For ease of illustration, a portion of the bony labyrinth 101 forming the vestibule 102 has been omitted from FIG. 1A, while the entire bony labyrinth 101 has been omitted from FIG. 1B.

Within the bony labyrinth 101 is the membranous labyrinth 103, which consists of the semicircular ducts 105, the otolith organs 111 (i.e., the utricle 112 and the saccule 114), and the cochlear duct 116. The membranous labyrinth 103 is filled with a fluid known as endolymph, and is surrounded by the perilymph of the bony labyrinth 101. The membranous labyrinth 103 is also suspended from the bony labyrinth 101 by fine connective tissue strands.

As shown, the bony labyrinth 101 includes three (3) semicircular canals 104, referred to as the superior or anterior semicircular canal 104(A), the posterior semicircular canal 104(B), and the horizontal or lateral semicircular canal 104(C). Within the superior semicircular canal 104(A) is the superior semicircular duct 105(B), within the posterior semicircular canal 104(B) is the posterior semicircular duct 105(B), and within the horizontal semicircular canal 104(C) is the horizontal semicircular duct 105(C). The semicircular ducts 105 are situated superoposterior to the vestibule 102 and each have a swelling at one end, known as an ampulla 110 (i.e., three ampullae are shown in FIGS. 1A and 1B, one for each duct 105).

The semicircular ducts 105(A), 105(B), and 105(C) are half-circular, interconnected tubes that are aligned approximately orthogonally to one another (i.e., at right angles to each other) so that they measure motions in all three planes. Specifically, lateral duct 105(C) is aligned roughly horizontally in the head, while the superior 105(A) and posterior ducts 105(B) are aligned roughly at a 45 degree angle to a vertical through the center of the individual's head. The semicircular ducts 105(A), 105(B), and 105(C) are each maximally sensitive to angular accelerations (head rotations) that lie in the plane of the duct. The result of this arrangement is that three semicircular ducts 105(A), 105(B), and 105(C) can uniquely specify the direction and amplitude of any arbitrary head rotation. That is, upon movement of the head, the flow of endolymph within the ducts 105 changes speed and/or direction. Sensory receptors in the ampullae 110 detect these changes, and send signals to the brain via the vestibular nerve 118 (FIG. 1B), allowing for the processing of balance.

As noted, the membranous labyrinth 103 also includes the utricle 112 and the saccule 114, which are collectively referred to as the otolith organs 111. The utricle 112 and the saccule 114 are two membranous sacs located in the vestibule 102, which detect movement or acceleration of the head in the horizontal and vertical planes, respectively (i.e., linear accelerations). The utricle 112 is the larger of the two, receiving the three semi-circular ducts 105. The saccule 114 is globular in shape and receives the cochlear duct 116.

The utricle 112 and the saccule 114 each contain a macula, which is an organ consisting of a patch of hair cells covered by a gelatinous membrane containing particles of calcium carbonate, called otoconia. Motions of the head cause the otoliths organs 111 to pull on these hair cells, stimulating the vestibular nerve 118, which allow the individual to perceive linear acceleration, both horizontally and vertically, and gravity control (i.e., gravitoinertial information).

The vestibular nerve 118 is one of the two branches of the vestibulocochlear nerve (the other being the auditory nerve 119), which functions to relay/transmit sensory information transmitted by the vestibular hair cells located in the two otolith organs (i.e., the utricle 112 and the saccule 114) and the three semicircular ducts 105 via the vestibular (Scarpa's) ganglion 121. Again, as noted, information from the otolith organs 111 reflects gravity and linear accelerations of the head, while information from the semicircular ducts 105 reflects rotational movement of the head.

The peripheral vestibular nerve fibers are generally divided into three branches. First, the superior vestibular nerve branch 126 passes through the foramina in the area vestibularis superior and ends in the utricle 112 and in the ampullae 110 of the superior and horizontal semicircular ducts 105(A) and 105(C), respectively. Second, the inferior vestibular nerve branch 128 traverse the foramina in the area vestibularis inferior and ends in the saccule 114. Third, the posterior vestibular nerve branch 130 runs through the foramen singulare and supplies the ampulla 110 of the posterior semicircular duct 105(B).

In general, the semicircular canals 104, ampullae 110, otolith organs 111, vestibular nerve 118, and the peripheral vestibular nerve fibers (i.e., the superior vestibular nerve branch 126, the inferior vestibular nerve branch 128, and the posterior vestibular nerve branch 130) are referred to herein as the "vestibular system" 127 of the recipient. Therefore, as used herein, delivery of electrical stimulation signals to the vestibular system 127 of the recipient may refer to the delivery of electrical stimulation signals (current signals) to any one or more of the semicircular canals 104, ampullae 110, otolith organs 111, vestibular nerve 118, the superior vestibular nerve branch 126, the inferior vestibular nerve branch 128, and/or the posterior vestibular nerve branch 130.

Also shown in FIG. 1A is the round window 120 and the oval window 122. The round window 120 and oval window 122 are the two openings from the middle ear (not shown) into the inner ear 100. The round window 120 is situated inferior to (below) and posterior to (behind) the oval window 122, from which it is separated by the promontory (rounded elevation). The oval window 122 is sealed by a membrane (oval window membrane) and leads from the middle ear to the vestibule of the inner ear 100. Vibrations that contact the tympanic membrane (ear drum) in the outer ear (not shown) travel through the three ossicles (i.e., malleus, incus, and stapes) of the middle ear and into the inner ear 100 via the oval window 122. That is, the oval window 122 is the intersection of the middle ear with the inner ear 100 and is directly contacted by the stapes. The round window 120 is also sealed by a membrane (round window membrane), which vibrates with opposite phase to vibrations entering the inner ear 100 through the oval window 122. The round window 120 allows fluid in the cochlea 106 to move.

As noted above, the inner ear 100 includes the semicircular ducts 105, the utricle 112, and the saccule 114, which collectively form what is referred to as the "peripheral vestibular apparatus" or the "peripheral vestibular system" 129. As noted, in an individual with a fully functional peripheral vestibular system, the recipient is able to sense head tilt and rotation during movement, which in turn helps the individual maintain balance, stabilize vision, etc. However, certain individuals may suffer from a balance disorder with complete or partial loss of vestibular system function/sensation in one or both ears. In general, a balance disorder is a condition in which an individual lacks the ability to control and/or maintain a proper (balanced) body position in a comfortable manner (i.e., the recipient experiences some sensation(s) of disbalance). Disbalance, sometimes referred to herein as balance problems, can manifest in a number of different manners, such as feelings of unsteadiness or dizziness, a feeling of movement, spinning, or floating, even though standing still or lying down, falling, difficulty walking in darkness without falling, blurred or unsteady vision, inability to stand or walk un-aided, etc. Balance disorders can be caused by certain health conditions, medications, aging, infections, head injuries, problems in the inner ear, problems with brain or the heart, problems with blood circulation, etc.

In general, a "balance prosthesis" or "balance implant" is a medical device that is configured to assist recipients (i.e., persons in which a balance prosthesis is implanted) that suffer from balance disorders. Although different balance prosthesis have been proposed to treat different types/causes of balance disorders, much conventional research has focused on devices, sometimes referred to as "vestibular implants" or "semi-circular canal stimulators," that stimulate the ampullas 110. Another type of balance prosthesis is sometimes referred to herein as a "vestibular nerve stimulator." As used herein, a vestibular nerve stimulator is a medical device that is configured to directly or indirectly electrically stimulate (i.e., deliver electrical stimulation signals (current signals) to) a recipient's otolith organs and/or vestibular nerve. That is, a vestibular nerve stimulator generates electrical stimulation signals that are specifically configured to evoke a response in the otolith organs and/or one or more segments of the vestibular nerve, such as the vestibular ganglion, inferior branch of the vestibular nerve, and/or the superior branch of the vestibular nerve.

Merely for ease of description, the techniques presented herein are primarily described herein with reference to a vestibular stimulation system that comprises a vestibular nerve stimulator. However, it is to be appreciated that the techniques presented herein may also be used with a variety of vestibular stimulation systems that include other types of balance prostheses that deliver electrical stimulation signals to a recipient's vestibular system.

In accordance with embodiments presented herein, a vestibular nerve stimulator includes a stimulating assembly, which comprises a plurality of electrodes. The stimulating assembly is implanted into the inner ear of the recipient adjacent to the otolith organs, via, for example, the recipient's oval window, through an anterior opening such as a stapedotomy, etc. Once implanted, the vestibular nerve stimulator is configured to electrically stimulate the vestibular system in a manner that improve the recipient's sense of balance (i.e., deliver electrical stimulation signals to the recipient's vestibular system).

As described further below, operation of a vestibular nerve stimulator in accordance with embodiments presented herein is set/controlled based on muscle responses potentially representative of one or more vestibular evoked myogenic potentials, namely muscle responses representative of one or both of the cervical vestibular evoked myogenic potential (cVEMP) and the ocular vestibular evoked myogenic potential (oVEMP). In particular, a vestibular stimulation system comprises a balance prosthesis, such as a vestibular nerve stimulator, that is configured to deliver electrical stimulation signals to the vestibular system of a recipient. The vestibular stimulation system also includes a vestibular evoked myogenic potential sensing arrangement that is configured to record, over a period of time following delivery of electrical stimulation signals to the recipient's vestibular system, muscle responses potentially representative of one or more vestibular evoked myogenic potentials. The recorded muscle responses are then used to control operation of the balance prosthesis (e.g., used to set one or more parameters of the electrical stimulation signals).

Figure 2A:
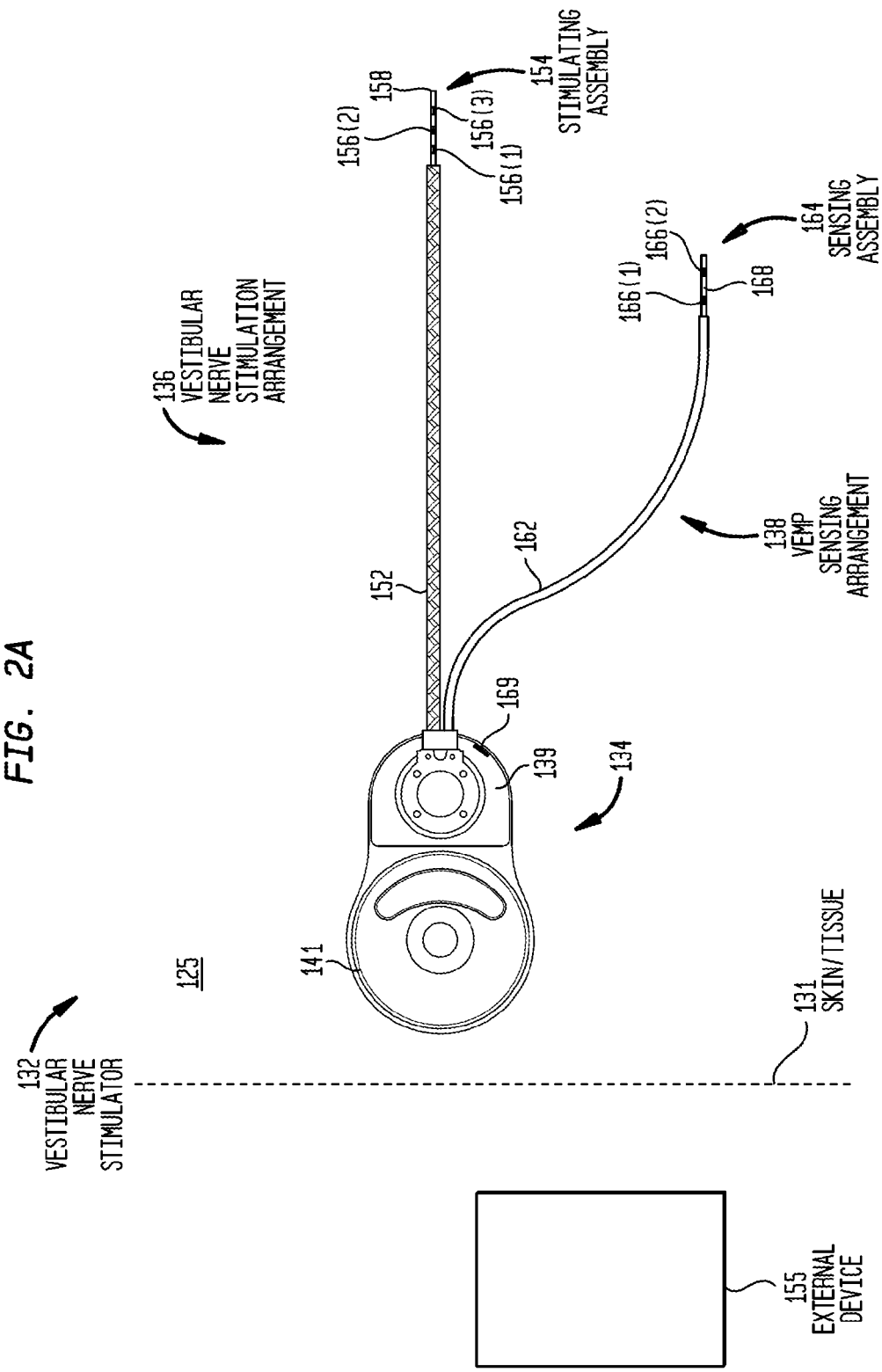
FIG. 2A is a schematic diagram illustrating a vestibular stimulation system, in accordance with certain embodiments presented herein.

FIGS. 2A and 2B illustrate further details of one example vestibular stimulation system 125 in accordance with embodiments presented herein. In this example, the vestibular stimulation system 125 comprises a vestibular nerve stimulator 132. More specifically, shown in FIG. 2A is a perspective view of the vestibular nerve stimulator 132, while FIG. 2B is a block diagram of the vestibular nerve stimulator 132. For ease of description, FIGS. 2A and 2B will be described together. Also for ease of illustration, certain components of the vestibular nerve stimulator 132 are described with reference to the inner ear 100 of FIGS. 1A and 1B.

As shown, the vestibular nerve stimulator 120 comprises an implant body (main module) 134, a vestibular nerve stimulation arrangement 136, and a vestibular evoked myogenic potential (VEMP) sensing arrangement 138, all of which are implantable within a recipient (i.e., implanted under the skin/tissue 131 of a recipient). The implant body 134 generally comprises a hermetically-sealed housing 139 in which Radio-Frequency (RF) interface circuitry 140, at least one processor 142, a memory device (memory) 144, a stimulator unit 146, a power source 148 (e.g., rechargeable battery), one or more sensors (e.g. motion sensors) 149, and a VEMP recording unit 150 are disposed. The implant body 134 also includes an internal/implantable coil 141 that is generally external to the housing 139, but which is connected to the RF interface circuitry 140 via a hermetic feedthrough (not shown in FIG. 2B). It is also to be appreciated that, although shown within housing 139, the VEMP recording unit 150 is functionally a component of the VEMP sensing arrangement 138 (i.e., reference to VEMP sensing arrangement includes the VEMP recording unit 150).

It is to be appreciated that the specific arrangement for the vestibular stimulation system 125 shown in FIGS. 2A and 2B is merely illustrative. As such, it is to be appreciated that vestibular nerve stimulators and associated systems may have a number of different arrangements in which, for example, the various functional components shown in FIG. 2B are implemented at one or a plurality of separate components, devices, etc. As such, the techniques presented herein may be implemented in vestibular stimulation systems having different arrangements, different components, etc., than that which is shown in FIGS. 2A and 2B.

In the example of FIGS. 2A and 2B, the processor 142 is configured to instruct the stimulator unit 146 to generate and deliver electrical stimulation signals to the recipient's vestibular system. The processor 142 may also perform other operations, include data logging, battery monitoring and low-battery alarm, etc. The stimulator unit 146 may include, for example, one or more current sources, switches, etc., that collectively operate to generate and deliver the electrical stimulation signals to the recipient via the vestibular nerve stimulation arrangement 136.

In certain examples, the electrical stimulation signals delivered to the recipient's vestibular system may be generated based on signals obtain by the one or more sensors 149. For example, the one or more sensors 149 may comprise one or more motion sensors configured to sense and generate outputs indicative of, for example, gravitoinertial accelerations (e.g., measure linear accelerations), rotational accelerations, etc. In such embodiments, the processor 142 may use the outputs generated by the one or more sensors 149 to control or otherwise set the parameters of the electrical stimulation signals delivered to the recipient.

The processor 142 and/or VEMP recording unit 150 may be formed by one or more processors (e.g., one or more Digital Signal Processors (DSPs), one or more uC cores, etc.), firmware, software, etc. arranged to perform operations described herein. That is, the processor 142 and/or VEMP recording unit 150 may be implemented as firmware elements, partially or fully implemented with digital logic gates in one or more application-specific integrated circuits (ASICs), partially in software, etc.

As shown in FIG. 2A, the vestibular nerve stimulation arrangement 136 comprises a lead 152 and a vestibular nerve stimulating (electrode) assembly 154. The stimulating assembly 154 comprises a plurality of electrodes 156 disposed in a carrier member 158 (e.g., a flexible silicone body). In this specific example, the stimulating assembly 154 comprises three (3) stimulation electrodes, referred to as stimulation electrodes 156(1), 156(2), and 156(3). As described further below, the stimulation electrodes 156(1), 156(2), and 156(3) function as an electrical interface for delivery of electrical stimulation signals to the recipient. It is to be appreciated that this specific embodiment with three stimulation electrodes is merely illustrative and that the techniques presented herein may be used with stimulating assemblies having different numbers of stimulation electrodes, stimulating assemblies having different lengths, etc.

As described elsewhere herein, the stimulating assembly 154 is configured such that a surgeon can implant the stimulating assembly adjacent the otolith organs 111 via, for example, the recipient's oval window 122. That is, the stimulating assembly 154 has sufficient stiffness and dynamics such that the stimulating assembly can be inserted through the oval window 122 and placed reliably within the bony labyrinth 101 adjacent the otolith organs 111 (e.g., sufficient stiffness to insert the stimulating assembly to the desired depth between the bony labyrinth 101 and the membranous labyrinth 103). In certain examples, the stimulating assembly 154 is configured to be placed adjacent the saccule 114.

In general, the stimulating assembly 154 has a stiffness allowing a single stroke atraumatic insertion to the required depth in the bone labyrinth 101. However, the stimulating assembly 154 may also have sufficient flexibility to deflect and avoid damage to the delicate anatomical structures of the inner ear 100.

The lead 152 has a configuration (e.g., length, flexibility, etc.) that allows for ease of surgical placement of the stimulating assembly 154 and that improves lead reliability (impact, fatigue, stress, etc.). In certain examples, the stimulating assembly 154 includes a removable or deformable stiffening member allowing placement of the stimulating assembly within the bony labyrinth 101.

As noted above, the vestibular nerve stimulator 132 comprises RF interface circuitry 140 and a power source 148 (e.g., one or more rechargeable batteries). In certain examples, vestibular nerve stimulation system 125 includes an external device 155 that is configured to charge/recharge the power source 148 through the inductive transfer of power via the RF interface circuitry 140. That is, although not shown in FIG. 2B, the external device 155 comprises an external coil configured to be inductively coupled with the implantable coil 141. When inductively coupled, the external coil and the implantable coil 141 form a closely-coupled wireless link by which power is transferred from a power source of the external device through the skin/tissue 131 of the recipient. In certain examples, the closely-coupled wireless link is a radio frequency (RF) link. However, various other types of energy transfer, such as infrared (IR), electromagnetic, capacitive and inductive transfer, may be used to transfer the power and/or data from the external device to the vestibular nerve stimulator 132.

As noted, in the example of FIGS. 2A and 2B, the vestibular nerve stimulator 132 also comprises the vestibular evoked myogenic potential (VEMP) sensing arrangement 138. As shown in FIG. 2A, the VEMP sensing arrangement 138 comprises a lead 162, a sensing (electrode) assembly 164, and the VEMP recording unit 150. The sensing assembly 164 comprises a plurality of electrodes 166 disposed in a carrier member 168 (e.g., a flexible silicone body). In this specific example, the stimulating assembly 164 comprises two (2) sense electrodes, referred to as sense electrodes 166(1) and 166(2). As described further below, the electrodes 166(1) and 166(2) operate with a ground electrode 169 to sense signals (muscle responses) that are potentially indicative of a vestibular evoked myogenic potential. In the example of FIG. 2A, the ground electrode 169 is located at implant body 134. However, it is to be appreciated that this specific embodiment of sense electrodes 166(1) and 166(2) and ground electrode 169 is merely illustrative and that the techniques presented herein may be used, for example, with the ground electrode 169 at a different location, stimulating assemblies having different lengths, etc.

The lead 162 has a configuration (e.g., length, flexibility, etc.) that allows for ease of surgical placement of the sensing assembly 164 and that improves lead reliability (impact, fatigue, stress, etc.). In certain examples, the stimulating assembly 164 includes a removable or deformable stiffening member allowing appropriate placement of the stimulating assembly.

As noted above, the processor 142 causes the stimulator unit 146 to generate and deliver electrical stimulation signals to the recipient's vestibular system. In general, depending, for example, on the implanted location of the stimulating assembly 154, the electrical stimulation signals are delivered to one or more of the otolith organs 111, i.e., the utricle 112 and/or the saccule 114. In accordance with embodiments presented herein, delivery of the electrical stimulation signals to the recipient via the utricle 112 and/or the saccule 114 is leveraged to control/set operation of the vestibular nerve stimulator 132, such as to set one or more parameters of the electrical stimulation signals delivered to the recipient (e.g., to provide a feedback/control loop for the electrical stimulation).

More specifically, in accordance with the techniques presented herein, the vestibular nerve stimulator 132 is configured to execute/implement a feedback loop based on an analysis of muscle responses (e.g., voltage signals recorded from muscles) that are associated with, and potentially indicative of, myogenic potentials that are evoked by a stimulation of the otolith organs 111. In general, two different vestibular evoked potentials may be triggered by the otolith organs 111, namely: (1) the cervical vestibular evoked myogenic potential (cVEMP) triggered by the saccule 114 and/or the inferior vestibular nerve branch 128; and (2) the ocular vestibular evoked myogenic potential (oVEMP) triggered by the utricle 112 and/or the superior vestibular nerve branch 126.

In the techniques presented, the VEMP sensing arrangement 138, potentially in combination with another sensing arrangement, is configured to capture/record responses from muscles within the recipient's body that are associated with vestibular evoked myogenic potentials. The muscle responses, which potentially represent and correspond to a vestibular evoked myogenic potential, are obtained during a time period following delivery of the electrical stimulation signals the recipient's vestibular system 127. Once recorded, the muscle responses can then be analyzed/evaluated. As used herein, reference to analysis of a vestibular evoked myogenic potential, such as the cervical vestibular evoked myogenic potential (cVEMP) or the ocular vestibular evoked myogenic potential (oVEMP) triggered, refers to the analysis of muscle responses (signals) obtained from the recipient's body during a measurement/recording time period. Additionally, as used herein, reference to analysis of a vestibular evoked myogenic potential includes reference to the analysis/evaluation of the absence of signals during a recording time period. The attributes of a recorded vestibular evoked myogenic potential (or the lack thereof) can then be used to, for example, control, adjust, or otherwise set parameters of the electrical stimulation signals delivered to the otolith organs 111. Provided below with reference to FIGS. 3A-3C and 4A-4CB are further details relating to operation of the VEMP sensing arrangement 138, including the VEMP recording unit 150, to record vestibular evoked myogenic potentials (muscle responses), as well as operation of the processor 142 to use the recorded vestibular evoked myogenic potentials to set parameters of the electrical stimulation signals. In particular, FIGS. 3A-3C illustrate operation of the VEMP sensing arrangement 138, VEMP recording unit 150, and the processor 142 with reference to the cervical vestibular evoked myogenic potential (cVEMP), while FIGS. 4A-4C illustrate operation of the VEMP sensing arrangement 138, VEMP recording unit 150, and the processor 142 with reference to the ocular vestibular evoked myogenic potential (oVEMP).

Figure 3A:
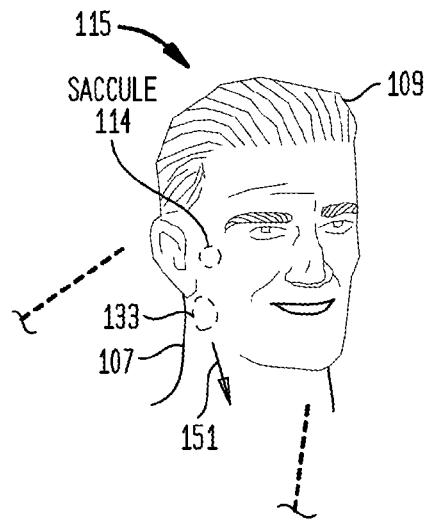
FIG. 3A is a perspective view of a head and neck of a recipient of a vestibular nerve stimulation system, in accordance with embodiments presented herein.

Referring first to FIG. 3A, shown is a perspective of the head 107 and neck 109 of a recipient 115 of the vestibular nerve stimulator 132. Also shown in FIG. 3A is the general location of the saccule 114 and the recipient's sternocleidomastoid muscle 133. FIG. 3B is schematic diagram illustrating the internal anatomy of the recipient 115, including anatomical structures of the inner ear 100 and the neck 109.

Figure 3B:
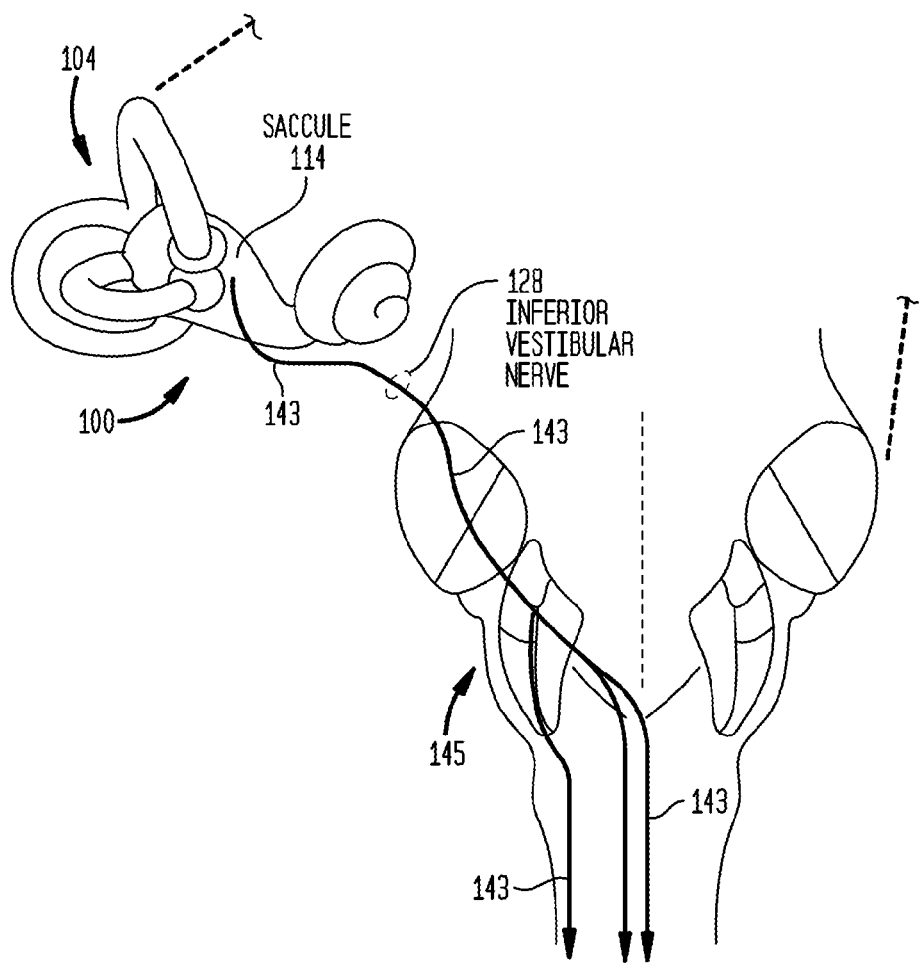
FIG. 3B is a schematic illustration of elements within the head and neck of the recipient of FIG. 3A.
Figure 3C:
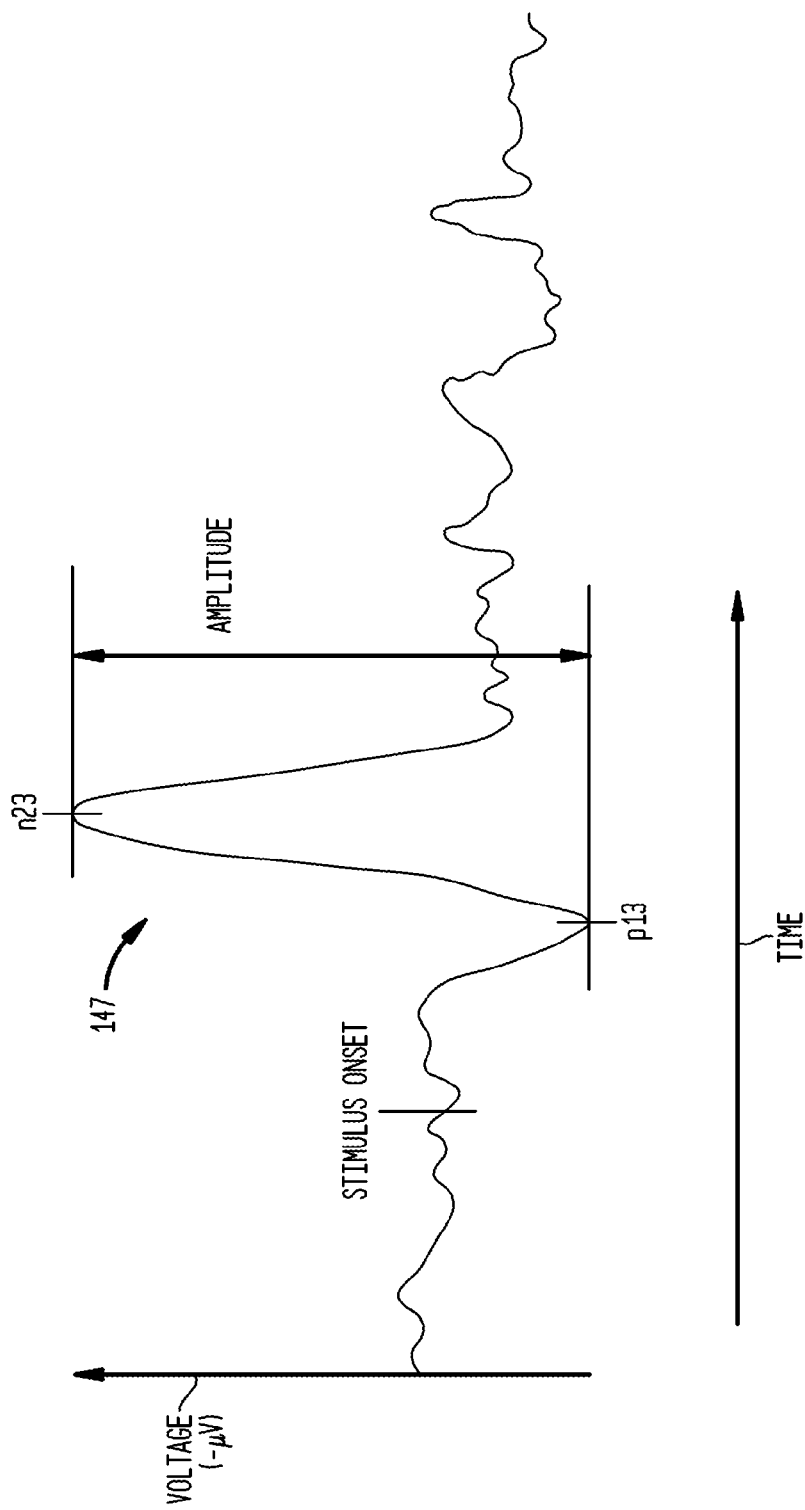
FIG. 3C is a diagram illustrating a characteristic cervical vestibular evoked myogenic potential (cVEMP)
Figure 4A:
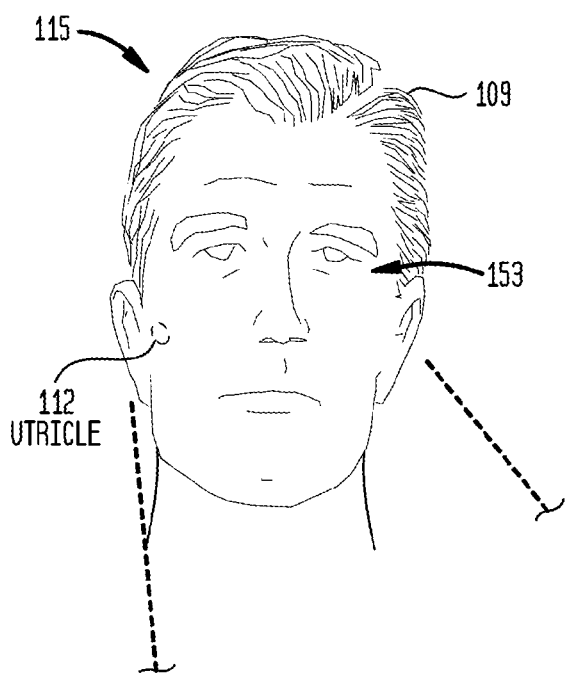
FIG. 4A is a perspective view of a head of a recipient of a vestibular nerve stimulation system, in accordance with embodiments presented herein.
Figure 4B:
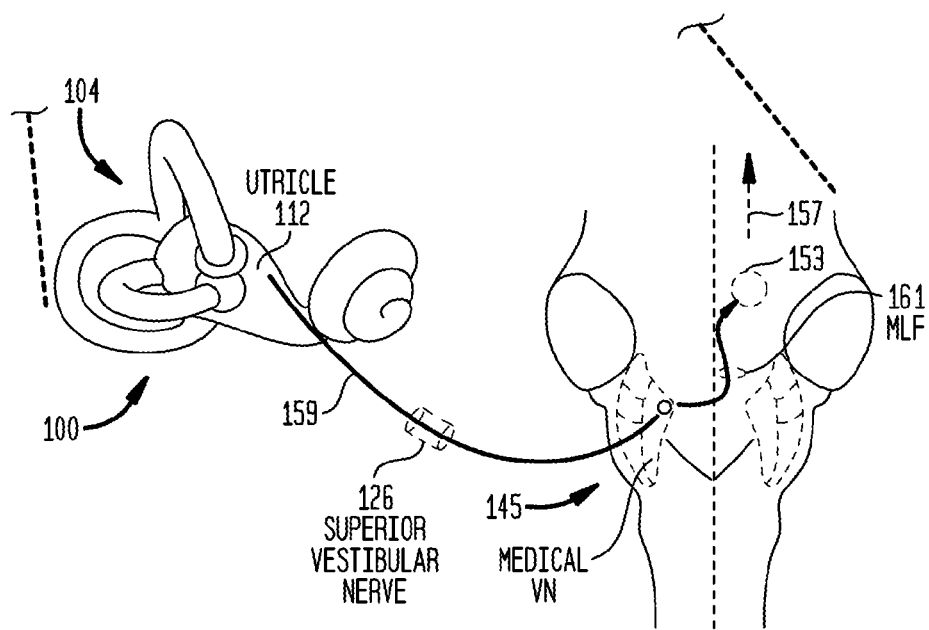
FIG. 4B is a schematic illustration of elements within the head of the recipient of FIG. 4A.
Figure 4C:
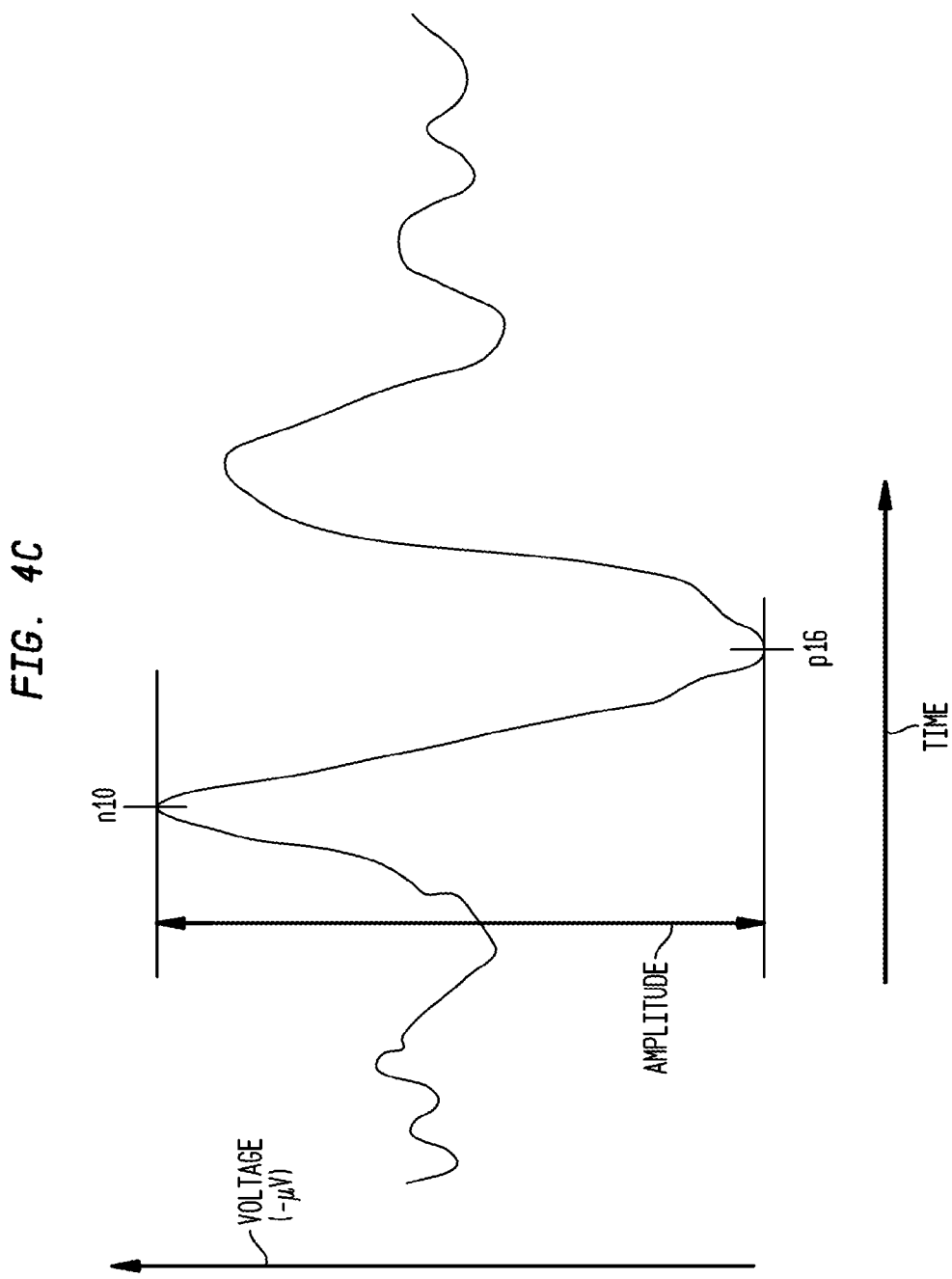
FIG. 4C is a diagram illustrating a characteristic ocular vestibular evoked myogenic potential (cVEMP)

For ease of illustration, the components of the vestibular nerve stimulator 132 have been omitted from FIGS. 3A and 3B. However, in general, the stimulating assembly 154 would be positioned within the recipient 115 so that the stimulation electrodes 156(1)-156(3) could deliver electrical stimulation to at least one of the saccule 114 and/or the inferior vestibular nerve branch 128. In addition, the sensing assembly 164 would be positioned within the recipient 115 so that the sense electrodes 166(1)-166(2) could record a cervical vestibular evoked myogenic potential (cVEMP) evoked within the sternocleidomastoid (SCM) muscle 133 (e.g., the sense electrodes 166(1)-166(2) would be positioned proximate to the sternocleidomastoid muscle 133).

The cervical vestibular evoked myogenic potential is an ipsilateral inhibitory reflex that is triggered when the saccule 114 is stimulated and, as noted, the cervical vestibular evoked myogenic potential can measured within the sternocleidomastoid muscle 133 (i.e., the responses in the sternocleidomastoid muscle 133). More specifically, as shown by arrow 143, electrical stimulation of the saccule 114 results in nerve impulse(s) carried through the ipsilateral inferior vestibular nerve branch 128 to the vestibular nucleus 145 from which the vestibulospinal (vestibulocollic) pathway (not shown) transmits a momentary inhibitory signal to the spinal accessory nerve supplying the ipsilateral sternocleidomastoid muscle 133.

FIG. 3C is a diagram illustrating a "target" or "characteristic" cervical vestibular evoked myogenic potential 147. That is, FIG. 3C illustrates voltages recorded from the recipient's sternocleidomastoid muscle 133 over a period of time.

As shown, the characteristic cervical vestibular evoked myogenic potential 147 comprises a biphasic voltage waveform with a voltage positivity (positivity) at about 13 milliseconds (ms) (referred to as a "p13-peak" or "p13") from (after) the stimulus onset (i.e., 13 milliseconds after the saccule 114 is stimulated) and a voltage negativity (negativity) at about 23 ms (referred to as an "n23-peak" or "n23") from the stimulus onset. That is, in the characteristic cervical vestibular evoked myogenic potential 147, the positivity and negativity have a relative order in which the positivity precedes the negativity, and a relative latency of 13 and 23 ms, respectively, to the delivery of the stimulation signals to the vestibular system 127.

As noted, sternocleidomastoid muscle responses, which are represented in FIG. 3A by arrow 151, are evoked in response to delivery of electrical stimulation to the saccule 114 by the vestibular nerve stimulator 132. The responses 151, which are sensed via the sense electrodes 166(1) and 166(2) with reference to ground electrode 169, are potentially representative of a cervical vestibular evoked myogenic potential. The VEMP recording unit 150 includes hardware (e.g., one or more amplifiers, filters, etc.) that captures/records the sternocleidomastoid muscle responses 151.

The processor 142 and/or another element can then analyze the sternocleidomastoid muscle responses 151 to, for example, determine whether a cervical vestibular evoked myogenic potential is present, determine attributes/characteristics of the cervical vestibular evoked myogenic potential, etc. This analysis of the sternocleidomastoid muscle responses 151, sometimes referred to herein as the analysis of a cervical vestibular evoked myogenic potential, can then be used to, for example, control, adjust, or otherwise set operation of the vestibular nerve stimulator 132. For example, the analysis of the sternocleidomastoid muscle responses 151 may be used to set parameters of subsequent electrical stimulation signals delivered to the recipient 115 by the vestibular nerve stimulator 132.

The analysis of the cervical vestibular evoked myogenic potential (i.e., of the recorded sternocleidomastoid muscle responses 151) may be performed in a number of different manners and, similarly, the results of the analysis may be used differently in different embodiments. In certain embodiments, the processor 142 is configured to determine the presence or absence of a cervical vestibular evoked myogenic potential following delivery of the electrical stimulation signals to the saccule 114 and/or the inferior nerve branch 128. For example, the processor 142 may be configured to determine whether the recorded sternocleidomastoid muscle responses 151 indicate a positivity followed by a negativity (e.g., analyze relative order of the voltage peaks). If both peaks are present, then the processor 142 may determine that the electrical stimulation signals evoked a cervical vestibular evoked myogenic potential.

In the above analysis, the processor 142 is generally configured to analyze the relative order of the voltage peaks of the recorded sternocleidomastoid muscle responses 151 to detect the presence of the positivity and the negativity. Additionally or alternatively, the processor 142 may be configured to perform additional voltage analysis and/or analyze other characteristics of the recorded sternocleidomastoid muscle responses 151. For example, in certain embodiments, to determine the presence or absence of a cervical vestibular evoked myogenic potential following delivery of the electrical stimulation signals to the saccule 114, the processor 142 may be configured to analyze the voltages of the recorded sternocleidomastoid muscle responses 151, along with timing (latency) information. In particular, the processor 142 may be configured to determine whether the recorded sternocleidomastoid muscle responses 151 not only indicate a positivity followed by a negativity, but also whether the responses indicate that the positivity occurs at about 13 milliseconds (ms) (i.e., indicate a p13-peak) from the stimulus and that the negativity occurs at about 23 ms (i.e., indicate an n23-peak) from the stimulus onset (i.e., the processor 142 analyzes latencies of p13 and n23).

The processor 142 may also or alternatively be configured to analyze other attributes of the recorded cervical vestibular evoked myogenic potential. For example, the processor 142 may evaluate the p13-n23 interamplitude, the p13-n23 interlatency, interaural difference of p13 and n23 latency, interaural amplitude difference (IAD) ratio, etc. of the recorded cervical vestibular evoked myogenic potential (i.e. in the sternocleidomastoid muscle responses 151).

In accordance with certain embodiments presented herein, the analysis of the cervical vestibular evoked myogenic potential (analysis of the sternocleidomastoid muscle responses 151) may be used as part of an initial calibration of the vestibular nerve stimulator 132. In one example, the cervical vestibular evoked myogenic potential may be used to initially evaluate the implanted location of the stimulating assembly 154 (e.g., to determine whether the stimulation electrodes 156(1)-156(3) are positioned so as to deliver stimulation to the saccule 114 and/or the inferior nerve branch 128). For example, if an cervical vestibular evoked myogenic potential is absent, or a recorded cervical vestibular evoked myogenic potential has unexpected attributes/features (e.g., attributes/features that are different than the characteristic cervical vestibular evoked myogenic potential 147), then the processor 142 may determine that the stimulation electrodes 156(1)-156(3) are not delivering stimulation, or an appropriate amount of stimulation, to the saccule 114 and/or the inferior nerve branch 128.

In one example, the analysis of the cervical vestibular evoked myogenic potential (analysis of the sternocleidomastoid muscle responses 151) may be used to initially set the level (magnitude/amplitude) of the electrical stimulation signals delivered to the saccule 114 and/or the inferior nerve branch 128 (i.e., set the current level for the stimulation signals). For example, if the cervical vestibular evoked myogenic potential is absent, the processor 142 may determine that the level of the stimulation signals is too low and should be increased.

Alternatively, if a recorded cervical vestibular evoked myogenic potential has unexpected attributes/features (e.g., attributes/features that are different than the characteristic cervical vestibular evoked myogenic potential 147), then the processor 142 may determine that the level of the stimulation signals is too low or too high and a current level adjustment may be initiated. The current level of the electrical stimulation signals may be incrementally adjusted up and/or down until, for example, the recorded cervical vestibular evoked myogenic potential has characteristics (e.g., peaks, peak latency, etc.) similar to the characteristic cervical vestibular evoked myogenic potential 147. In comparison to the evaluation of the implanted location of the stimulating assembly 154, above, the evaluation of the amplitude of the electrical stimulation signals may analyze different attributes, may place greater emphasis on certain differences to a target cervical vestibular evoked myogenic potential, etc.

The initial evaluation of location and/or the amplitude of the electrical stimulation signals are merely illustrative of initial calibrations that may be performed for the vestibular nerve stimulator 132 based on a recorded (or lack of recorded) cervical vestibular evoked myogenic potential. For example, the recorded cervical vestibular evoked myogenic potential may also be used to initially set other parameters of the electrical stimulation signals, such as the frequency, pulse rate, pulse gap, etc. of the electrical stimulation signals. As such, it is to be appreciated that the techniques presented herein are not limited to the above two exemplary calibrations based on a recorded cervical vestibular evoked myogenic potential.

In accordance with certain embodiments presented herein, a cervical vestibular evoked myogenic potential may also be used as a control mechanism (control loop) to dynamically adjust (e.g., in real-time) parameters of the electrical stimulation signals. For example, during operation, the processor 142 could be configured to continually, periodically/regularly, randomly, pseudo-randomly, etc. analyze the cervical vestibular evoked myogenic potential obtained via the VEMP sensing arrangement 138 and the VEMP recording unit 150. In such examples, the analysis of the cervical vestibular evoked myogenic potential may be used to adjust one or more of the amplitude, frequency, pulse rate, pulse gap, etc. of the electrical stimulation signals delivered to the recipient. The vestibular nerve stimulator 132 (e.g. processor 142) may adjust parameters of the electrical stimulation signals, for example, when attributes of the cervical vestibular evoked myogenic potential change, when attributes of the cervical vestibular evoked myogenic potential are different from a previously recorded cervical vestibular evoked myogenic potential, when attributes of the cervical vestibular evoked myogenic potential are different from the characteristic cervical vestibular evoked myogenic potential 147, etc.

Referring next to FIG. 4A, shown is a perspective of the head 107 of the recipient 115 of the vestibular nerve stimulator 132. Also shown in FIG. 4A is the general location of the utricle 112 and the recipient's extra ocular muscles 153. FIG. 4B is schematic diagram illustrating the internal anatomy of the recipient 115, including anatomical structures of the inner ear 100.

For ease of illustration, the components of the vestibular nerve stimulator 132 have been omitted from FIGS. 4A and 4B. However, in general, in this example, the stimulating assembly 154 would be positioned within the recipient 115 so that the stimulation electrodes 156(1)-156(3) could deliver electrical stimulation to at least one of the utricle 112 and/or the superior vestibular nerve branch 126. In addition, the sensing assembly 164 would be positioned within the recipient 115 so that the sense electrodes 166(1)-166(2) could record an ocular vestibular evoked myogenic potential (oVEMP) evoked within the extra ocular muscles 153 (e.g., the sense electrodes 166(1)-166(2) would be positioned proximate to the extra ocular muscles 153).

The ocular vestibular evoked myogenic potential is a contralateral (crossed) excitatory reflex that is triggered when the utricle 112 is stimulated which, as noted, can measured within the contralateral extra ocular muscles 153 (i.e., the responses in the extra ocular muscles 153). More specifically, as shown by arrow 159, electrical stimulation of the utricle 112 results in nerve impulse(s) carried through the ipsilateral superior vestibular nerve branch 126 to the to the ipsilateral vestibular nucleus 145 from which the signals cross the midline and travel up the medial longitudinal fasciculus 161 to send an excitatory stimulus to the inferior oblique subnucleus of the extra ocular muscles 153 (the oculomotor nucleus), causing momentary contraction which is sensed by the sense electrodes 166(1) and 166(2), and averaged repetitively.

FIG. 4C is a diagram illustrating a "target" or "characteristic" ocular vestibular evoked myogenic potential 167. That is, FIG. 4C illustrates voltages recorded from the recipient's extra ocular muscles 153 over a period of time.

As shown, the characteristic ocular vestibular evoked myogenic potential 167 comprises a voltage waveform with a voltage negativity (negativity) at about 10 milliseconds (ms) (referred to as a "n10-peak" or "n10") from (after) the stimulus onset (i.e., 10 milliseconds after the utricle 112 is stimulated) and a voltage positivity (positivity) at about 15 ms (referred to as a "p15-peak" or "p15") or at about 16 ms (referred to as a "p16-peak" or "p16) from the stimulus onset. In general, for the oVEMP the primary indicator may be the n10 peak. For ease of description, the examples are described herein with reference to an n10 and a p15. However, the oVEMP may also occur with an n10 and a p16.

As noted, extra ocular muscles responses, which are represented in FIG. 4B by arrow 157, are evoked in response to delivery of electrical stimulation to the utricle 112 by the vestibular nerve stimulator 132. The responses 157, which are sensed via the sense electrodes 166(1) and 166(2) with reference to ground electrode 169, are potentially representative of an ocular vestibular evoked myogenic potential. The VEMP recording unit 150 includes hardware (e.g., one or more amplifiers, filters, etc.) that captures/records the extra ocular muscle responses 157.

The processor 142 and/or another element can then analyze the extra ocular muscle responses 157 to, for example, determine whether an ocular vestibular evoked myogenic potential is present, determine attributes/characteristics of the ocular vestibular evoked myogenic potential, etc. This analysis of the extra ocular muscle responses 157, sometimes referred to herein as the analysis of an ocular vestibular evoked myogenic potential, can then be used to, for example, control, adjust, or otherwise set operation of the vestibular nerve stimulator 132. For example, analysis of the extra ocular muscle responses 157 can be used to set one or more parameters of subsequent electrical stimulation signals delivered to the vestibular system 127 of the recipient 115 by the vestibular nerve stimulator 132.

The analysis of the ocular vestibular evoked myogenic potential (i.e., of the recorded extra ocular muscle responses 157) may be performed in a number of different manners and, similarly, the results of the analysis may be used differently in different embodiments. In certain embodiments, the processor 142 is configured to determine the presence or absence of an ocular vestibular evoked myogenic potential following delivery of the electrical stimulation signals to the utricle 112 and/or the superior nerve branch 126. For example, the processor 142 may be configured to determine whether the recorded extra ocular muscle responses 157 indicate a negativity followed by a positivity. If both peaks are present, then the processor 142 may determine that the electrical stimulation signals evoked an ocular vestibular evoked myogenic potential.

In the above analysis, the processor 142 is generally configured to analyze the voltages of the recorded extra ocular muscle responses 157 to detect the presence of the negativity and the positivity. Additionally or alternatively, the processor 142 may be configured to perform additional voltage analysis and/or analyze other characteristics of the recorded extra ocular muscle responses 157. For example, in certain embodiments, to determine the presence or absence of an ocular vestibular evoked myogenic potential following delivery of the electrical stimulation signals to the utricle 112, the processor 142 may be configured to analyze the voltages of the recorded extra ocular muscle responses 157, along with timing (latency) information. In particular, the processor 142 may be configured to determine whether that the recorded extra ocular muscle responses 157 not only indicate a negativity followed by a positivity, but also whether the responses indicate that the negativity occurs at about 10 milliseconds (ms) (i.e., indicate an n10-peak) from the stimulus and that the positivity occurs at about 15 ms (i.e., indicate a p15-peak) from the stimulus onset (i.e., the processor 142 analyzes latencies of n10 and p15).

The processor 142 may also or alternatively be configured to analyze other attributes of the recorded ocular vestibular evoked myogenic potential. For example, the processor 142 may evaluate the n10-p15 interamplitude, the n10-p15 interlatency, interaural difference of n10 and p15 latency, interaural amplitude difference (IAD) ratio, etc. of the recorded ocular vestibular evoked myogenic potential (i.e. in the extra ocular muscle responses 157).

In accordance with certain embodiments presented herein, the analysis of the ocular vestibular evoked myogenic potential (analysis of the extra ocular muscle responses 157) may be used as part of an initial calibration of the vestibular nerve stimulator 132. In one example, the ocular vestibular evoked myogenic potential may be used to initially evaluate the implanted location of the stimulating assembly 154 (e.g., to determine whether the stimulation electrodes 156(1)-156(3) are positioned so as to deliver stimulation to the utricle 112 and/or the superior nerve branch 126). For example, if an ocular vestibular evoked myogenic potential is absent, or a recorded ocular vestibular evoked myogenic potential has unexpected attributes/features (e.g., attributes/features that are different than the characteristic ocular vestibular evoked myogenic potential 167), then the processor 142 may determine that the stimulation electrodes 156(1)-156(3) are not delivering stimulation, or an appropriate amount of stimulation, to the utricle 112 and/or the superior nerve branch 126.

In one example, the analysis of the ocular vestibular evoked myogenic potential (analysis of the extra ocular muscle responses 157) may be used to initially set the level (magnitude/amplitude) of the electrical stimulation signals delivered to the utricle 112 and/or the superior nerve branch 126 (i.e., set the current level for the stimulation signals). For example, if the ocular vestibular evoked myogenic potential is absent, the processor 142 may determine that the level of the stimulation signals is too low and should be increased.

Alternatively, if a recorded ocular vestibular evoked myogenic potential has unexpected attributes/features (e.g., attributes/features that are different than the characteristic ocular vestibular evoked myogenic potential 167), then the processor 142 may determine that the level of the stimulation signals is too low or too high and a current level adjustment may be initiated. The current level of the electrical stimulation signals may be incrementally adjusted up and/or down until, for example, the recorded ocular vestibular evoked myogenic potential has characteristics (e.g., peaks, peak latency, etc.) similar to the characteristic ocular vestibular evoked myogenic potential 167. In comparison to the evaluation of the implanted location of the stimulating assembly 154, above, the evaluation of the amplitude of the electrical stimulation signals may analyze different attributes, may place greater emphasis on certain differences to a target ocular vestibular evoked myogenic potential, etc.

The initial evaluation of location and/or the amplitude of the electrical stimulation signals are merely illustrative of initial calibrations that may be performed for the vestibular nerve stimulator 132 based on a recorded (or lack of recorded) ocular vestibular evoked myogenic potential. For example, the recorded ocular vestibular evoked myogenic potential may also be used to initially set other parameters of the electrical stimulation signals, such as the frequency, pulse rate, pulse gap, etc. of the electrical stimulation signals. As such, it is to be appreciated that the techniques presented herein are not limited to the above two exemplary calibrations based on a recorded ocular vestibular evoked myogenic potential.

In accordance with certain embodiments presented herein, an ocular vestibular evoked myogenic potential may also be used as a control mechanism (control loop) to dynamically adjust (e.g., in real-time) parameters of the electrical stimulation signals. For example, during operation, the vestibular nerve stimulator 132 could be configured to continually, periodically/regularly, randomly, pseudo-randomly, etc. analyze the ocular vestibular evoked myogenic potential obtained via the VEMP sensing arrangement 138 and the VEMP recording unit 150. In such examples, the analysis of the ocular vestibular evoked myogenic potential may be used to adjust one or more of the amplitude, frequency, pulse rate, pulse gap, etc. of the electrical stimulation signals delivered to the recipient. The vestibular nerve stimulator 132 (e.g. processor 142) may adjust parameters of the electrical stimulation signals, for example, when attributes of the ocular vestibular evoked myogenic potential change, when attributes of the ocular vestibular evoked myogenic potential are different from a previously recorded ocular vestibular evoked myogenic potential, when attributes of the ocular vestibular evoked myogenic potential are different from the characteristic ocular vestibular evoked myogenic potential 167, etc.

More ease of description, FIGS. 3A-3C and 4A-4C have been described with reference to the example vestibular stimulation system 125 of FIGS. 2A and 2B. In this example arrangement, the nerve stimulator 132 is a self-contained device that includes the sensing arrangement, the hardware/software configured to record and analyze the vestibular evoked myogenic potentials, as well as the hardware/software configured to adjust parameters of the electrical stimulation delivered to the recipient based on the analysis of the vestibular evoked myogenic potentials. However, it is to be appreciated that the self-contained arrangement of FIGS. 2A and 2B is merely illustrative and that the techniques presented herein may be implemented in systems having different arrangements where the sensing, analysis, and stimulation control/adjustment may be split across different devices in different combinations.

Figure 5:
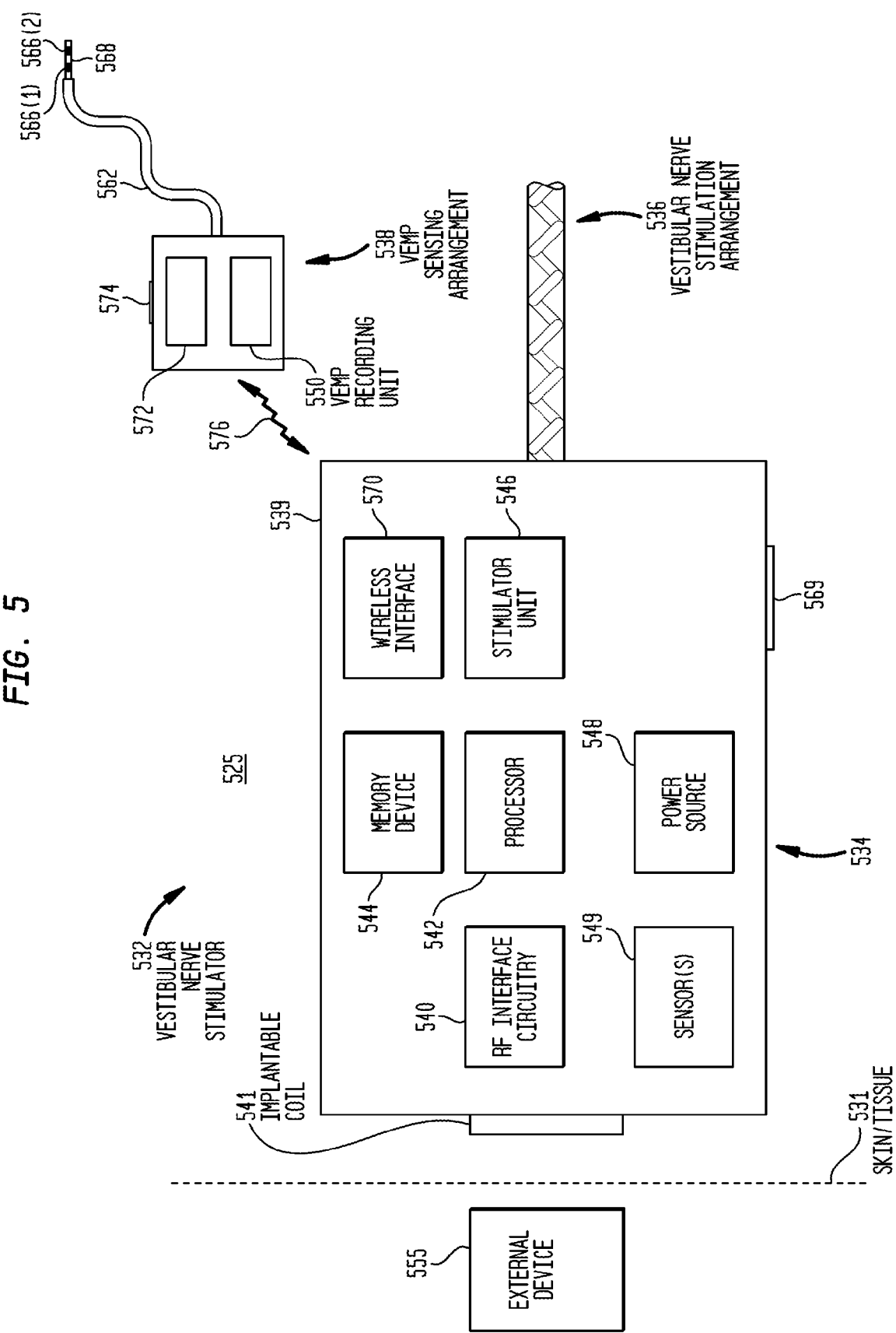
FIG. 5 is a simplified block diagram of another vestibular stimulation system, in accordance with certain embodiments presented herein.

For example, FIG. 5 is a block diagram of an example vestibular stimulation system 525 in accordance with embodiments presented herein. In this example, the vestibular stimulation system 525 comprises a vestibular nerve stimulator 532 and a separate vestibular evoked myogenic potential (VEMP) sensing arrangement 538.

The vestibular nerve stimulator 532 is similar to vestibular nerve stimulator 132 of FIGS. 2A and 2B in that it comprises an implant body 534 and a vestibular nerve stimulation arrangement 536, both of which are implantable within a recipient (i.e., implanted under the skin/tissue 531 of a recipient). Again, similar to vestibular nerve stimulator 132, the implant body 534 generally comprises a hermetically-sealed housing 539 in which Radio-Frequency (RF) interface circuitry 540, at least one processor 542, a memory device (memory) 544, a stimulator unit 546, a power source 548 (e.g., rechargeable battery), and one or more sensors (e.g. motion sensors) 549 are disposed. The implant body 534 also includes a ground electrode 569 disposed on the housing 539, and an internal/implantable coil 541 that is generally external to the housing 539, but which is connected to the RF interface circuitry 540 via a hermetic feedthrough (not shown in FIG. 5).

In addition to the above components, the vestibular nerve stimulator 532, namely the implant body 534, further includes a wireless interface 570. As described further below, the wireless interface 570 is configured for wireless communication with, for example, the VEMP sensing arrangement 538 over a channel operated in accordance with a short-range wireless standard (i.e., a non-closely coupled wireless link).

The processor 542 is configured to instruct the stimulator unit 546 to generate and deliver electrical stimulation signals to the recipient's vestibular system via the vestibular nerve stimulation arrangement 536. In certain examples, the electrical stimulation signals delivered to the recipient's vestibular nerve may be generated based on signals obtain by the one or more sensors 549 (e.g., motion sensors).

Although not shown in FIG. 5, the vestibular nerve stimulation arrangement 536 may include the same or similar components as vestibular nerve stimulation arrangement 136 of FIGS. 2A and 2B. That is, the nerve stimulation arrangement 536 may comprise a lead and a vestibular nerve stimulating (electrode) assembly, which includes a plurality of stimulation electrodes disposed in a carrier member (e.g., a flexible silicone body). As described elsewhere herein, the stimulation electrodes function as an electrical interface for delivery of electrical stimulation signals to the recipient.

The vestibular nerve stimulator 532 comprises RF interface circuitry 540 and a power source 548 (e.g., one or more rechargeable batteries). In certain examples, vestibular nerve stimulation system 525 includes an external device 555 that is configured to charge/recharge the power source 548 through the inductive transfer of power via the RF interface circuitry 540.

As noted, the vestibular stimulation system 525 also comprises the vestibular evoked myogenic potential (VEMP) sensing arrangement 538. As shown in FIG. 5, the VEMP sensing arrangement 538 comprises a sensor body 571, a lead 562 and a sensing (electrode) assembly 564. In the example of FIG. 5, the VEMP sensing arrangement 538, namely the sensor body 571, includes a vestibular evoked myogenic potential (VEMP) recording unit 550 and a wireless interface 574.

The sensing assembly 564 comprises a plurality of electrodes 566 disposed in a carrier member 568 (e.g., a flexible silicone body). In this specific example, the stimulating assembly 564 comprises two (2) sense electrodes, referred to as sense electrodes 566(1) and 566(2). As described further below, the electrodes 566(1) and 566(2) operate with a ground electrode 572 to sense a vestibular evoked myogenic potential. In the example of FIG. 5, the ground electrode 572 is located at the sensor body 571. However, it is to be appreciated that this specific embodiment of sense electrodes 566(1) and 566(2) and ground electrode 572 is merely illustrative and that the techniques presented herein may be used, for example, with the ground electrode 572 at a different location, stimulating assemblies having different lengths, etc.

As noted above, the processor 542 causes the stimulator unit 546 to generate and deliver electrical stimulation signals to the recipient's vestibular system. In general, depending, for example, on the implanted location of the stimulating assembly 554, the electrical stimulation signals are delivered to one or more of the otolith organs i.e., the utricle and/or the saccule. In accordance with embodiments presented herein, delivery of the electrical stimulation signals to the recipient via the utricle and/or the saccule is leveraged to control operation of the vestibular nerve stimulator 532 (e.g., set one or more parameters of the electrical stimulation signals delivered to the recipient's vestibular system.

More specifically, in the example of FIG. 5, the sense electrodes 566(1) and 566(2) are configured (e.g., positioned and arranged) so as to record muscle responses potentially representative of one or more vestibular evoked myogenic potentials triggered in response to delivery of electrical stimulation signals to a recipient's vestibular system via vestibular nerve stimulation arrangement 536. That is, similar to the embodiments described above with reference to FIGS. 3A-3C and/or FIGS. 4A-4C, the sense electrodes 566(1) and 566(2) are configured to sense responses within the recipient's sternocleidomastoid muscle or extra ocular muscle to record muscle responses associated within the cervical vestibular evoked myogenic potential (cVEMP) or the ocular vestibular evoked myogenic potential (oVEMP). The VEMP recording unit 550 includes hardware (e.g., one or more amplifiers, filters, etc.) that captures/records the sternocleidomastoid muscle or extra ocular muscle responses.

The muscle responses recorded in/by the sense electrodes 566(1) and 566(2) are provided to the vestibular nerve stimulator 532 via a short-range wireless communication channel (wireless channel) 575 formed between the wireless interfaces 570 and 572. The wireless channel 575 may be, for example, a standardized wireless channel, such as Bluetooth®, Bluetooth® Low Energy (BLE) or other channel interface making use of any number of standard wireless streaming protocols. Bluetooth® is a registered trademark owned by the Bluetooth® SIG. In other examples, the wireless channel 575 may be a proprietary channel that makes use of a proprietary protocol for wireless streaming of the recorded responses.

Once received by the wireless interface 570, the responses recorded by the VEMP sensing arrangement 538 may be analyzed by the processor 542 in, for example, a similar manner as described above with reference to FIGS. 3A-3C and/or FIGS. 4A-4C. That is, the processor 542 is configured to, for example, set parameters of the electrical stimulation signals delivered to the recipient via the vestibular nerve stimulation arrangement 536 based on an analysis of the vestibular evoked myogenic potentials (analysis of the recorded muscle responses). In this way, the vestibular stimulation system 525 is configured to execute/implement a feedback loop based on an analysis of vestibular evoked myogenic potentials that are evoked by a stimulation of the otolith organs.

FIG. 5 illustrates an example arrangement in which one VEMP sensing arrangement 538 is used to capture responses associated with vestibular evoked myogenic potentials. However, it is to be appreciated that, in an alternative embodiment, two VEMP sensing arrangements 538 may be provided. In such arrangements, a first one of the VEMP sensing arrangements 538 is configured to record sternocleidomastoid muscle responses associated the cervical vestibular evoked myogenic potential, while a second one of the VEMP sensing arrangements 538 is configured to record the extra ocular muscle responses associated with the ocular vestibular evoked myogenic potential. Both of the VEMP sensing arrangements 538 would provide their associated recorded responses to the vestibular nerve stimulator 532 via wireless interface 570 for subsequent analysis by the processor 542. In such an example, the processor 542 may be configured to execute the analysis of FIGS. 3A-3C and that of FIGS. 4A-4C to set the stimulation parameters, as described above.

Figure 6:
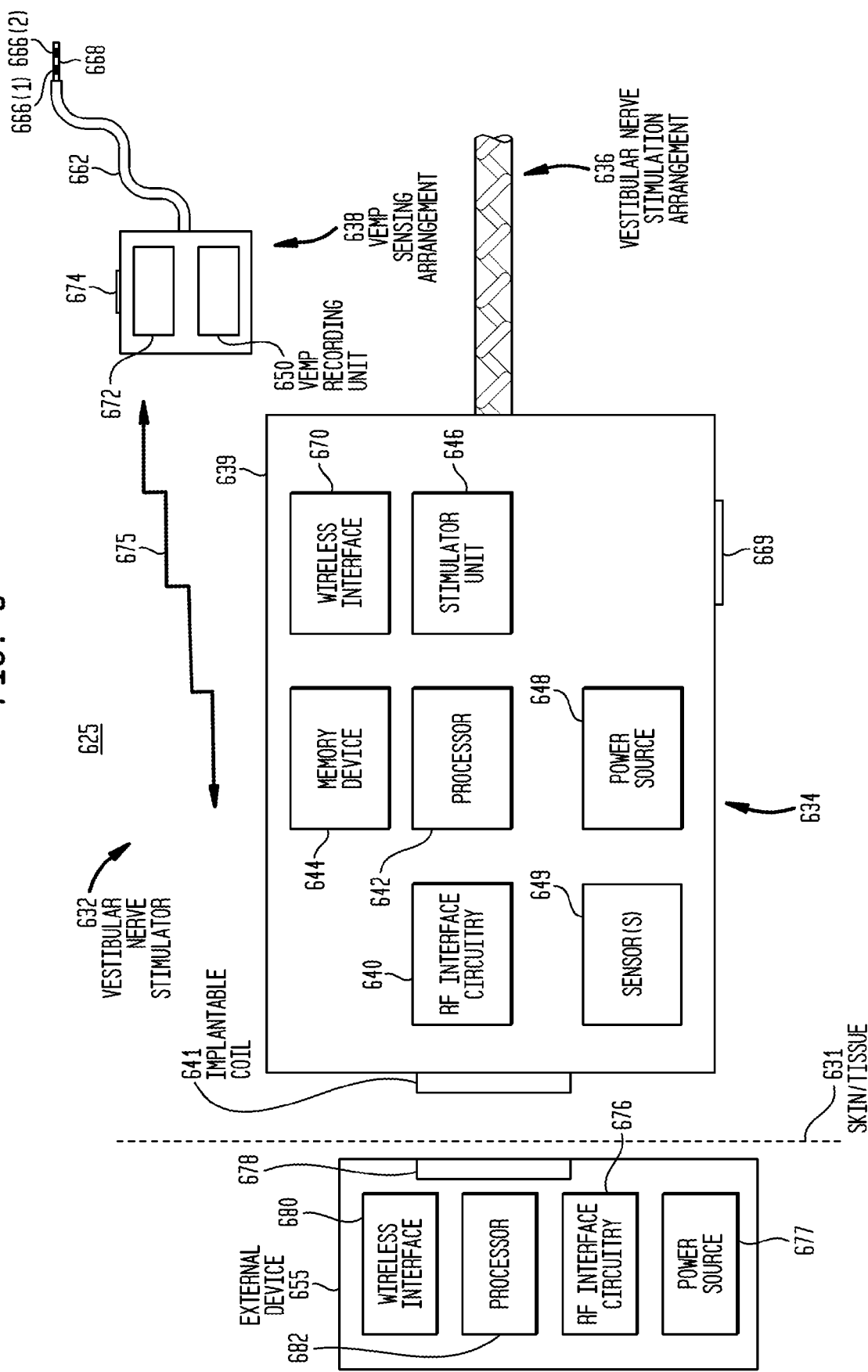
FIG. 6 is a simplified block diagram of another vestibular stimulation system, in accordance with certain embodiments presented herein.

FIG. 6 is a block diagram of another example vestibular stimulation system 625 in accordance with embodiments presented herein. In this example, the vestibular stimulation system 625 comprises a vestibular nerve stimulator 632, a separate vestibular evoked myogenic potential (VEMP) sensing arrangement 638, and an external device 655. In contrast to the prior embodiment, the external device 655 is part of the feedback/control loop used to, for example, set electrical stimulation parameters based on the vestibular evoked myogenic potentials.

More specifically, the external device 655 comprises Radio-Frequency (RF) interface circuitry 676, a power source (e.g., one or more batteries) 677, a wireless interface 680, and at least one processor 682. The vestibular nerve stimulator 632 is similar to vestibular nerve stimulator 532 of FIG. 5 in that it comprises an implant body 634 and a vestibular nerve stimulation arrangement 636, both of which are implantable within a recipient (i.e., implanted under the skin/tissue 631 of a recipient).

Again, similar to vestibular nerve stimulator 532, the implant body 634 generally comprises a hermetically-sealed housing 639 in which Radio-Frequency (RF) interface circuitry 640, at least one processor 642, a memory device (memory) 644, a stimulator unit 646, a power source 648 (e.g., rechargeable battery), and one or more sensors (e.g., motion sensors) 649, and a wireless interface 670 are disposed. The implant body 634 also includes a ground electrode 669 disposed on the housing 639, and an internal/implantable coil 641 that is generally external to the housing 639, but which is connected to the RF interface circuitry 640 via a hermetic feedthrough (not shown in FIG. 6).

The processor 642 is configured to instruct the stimulator unit 646 to generate and deliver electrical stimulation signals to the recipient's vestibular system via the vestibular nerve stimulation arrangement 636. In certain examples, the electrical stimulation signals delivered to the recipient's vestibular nerve may be generated based on signals obtain by the one or more sensors 649 (e.g., motion sensors).

Although not shown in FIG. 6, the vestibular nerve stimulation arrangement 636 may include the same or similar components as vestibular nerve stimulation arrangement 136 of FIGS. 2A and 2B. That is, the nerve stimulation arrangement 636 may comprise a lead and a vestibular nerve stimulating (electrode) assembly, which includes a plurality of stimulation electrodes disposed in a carrier member (e.g., a flexible silicone body). As described elsewhere herein, the stimulation electrodes function as an electrical interface for delivery of electrical stimulation signals to the recipient.

As noted above, the vestibular nerve stimulator 632 comprises RF interface circuitry 640 and a power source 648 (e.g., one or more rechargeable batteries). In certain examples, vestibular nerve stimulation system 625 includes an external device 655 that is configured to charge/recharge the power source 648 through the inductive transfer of power via the RF interface circuitry 640. That is, external coil 678 of external device 655 is configured to be inductively coupled with the implantable coil 641. When inductively coupled, the external coil 678 and the implantable coil 641 form a closely-coupled wireless link over which the RF interface circuitry 676 can transfer power (from power source 677) to the RF interface circuitry 640. The power received at the RF interface circuitry 640 can then be used to charge/recharge the power source 648.

As noted, the vestibular stimulation system 625 also comprises the vestibular evoked myogenic potential (VEMP) sensing arrangement 638. As shown in FIG. 6, the VEMP sensing arrangement 638 comprises a sensor body 671, a lead 662 and a sensing (electrode) assembly 664. In the example of FIG. 6, the VEMP sensing arrangement 638, namely the sensor body 671, includes a vestibular evoked myogenic potential (VEMP) recording unit 650 and a wireless interface 674.

The sensing assembly 664 comprises a plurality of electrodes 666 disposed in a carrier member 668 (e.g., a flexible silicone body). In this specific example, the stimulating assembly 664 comprises two (2) sense electrodes, referred to as sense electrodes 666(1) and 666(2). As described further below, the electrodes 666(1) and 666(2) operate with a ground electrode 672 to sense a vestibular evoked myogenic potential. In the example of FIG. 6, the ground electrode 672 is located at the sensor body 671. However, it is to be appreciated that this specific embodiment of sense electrodes 666(1) and 666(2) and ground electrode 672 is merely illustrative and that the techniques presented herein may be used, for example, with the ground electrode 672 at a different location, stimulating assemblies having different lengths, etc.

As noted above, the processor 642 causes the stimulator unit 646 to generate and deliver electrical stimulation signals to the recipient's vestibular system. In general, depending, for example, on the implanted location of the stimulating assembly 654, the electrical stimulation signals are delivered to one or more of the otolith organs, i.e., the utricle and/or the saccule. In accordance with embodiments presented herein, delivery of the electrical stimulation signals to the recipient via the utricle and/or the saccule is leveraged to control/set operation of the vestibular nerve stimulator 632 (e.g., set one or more parameters of the electrical stimulation signals delivered to the vestibular system).

More specifically, in the example of FIG. 6, the sense electrodes 666(1) and 666(2) are configured (e.g., positioned and arranged) so as to record muscle responses potentially indicative of a vestibular evoked myogenic potential triggered in response to delivery of electrical stimulation signals to a recipient's vestibular system via vestibular nerve stimulation arrangement 636. That is, similar to the embodiments described above with reference to FIGS. 3A-3C and/or FIGS. 4A-4C, the sense electrodes 666(1) and 666(2) are configured to sense responses within the recipient's sternocleidomastoid muscle or extra ocular muscle associated with the cervical vestibular evoked myogenic potential (cVEMP) or the ocular vestibular evoked myogenic potential (oVEMP), respectively. The VEMP recording unit 650 includes hardware (e.g., one or more amplifiers, filters, etc.) that captures/records the sternocleidomastoid muscle or extra ocular muscle responses.

The responses recorded by the sense electrodes 666(1) and 666(2) are provided to the external device 655 via a short-range wireless communication channel (wireless channel) 675 formed between the wireless interfaces 670 and 672. The wireless channel 675 may be, for example, a standardized wireless channel, such as Bluetooth®, Bluetooth® Low Energy (BLE) or other channel interface making use of any number of standard wireless streaming protocols. Bluetooth® is a registered trademark owned by the Bluetooth® SIG. In other examples, the wireless channel 675 may be a proprietary channel that makes use of a proprietary protocol for wireless streaming of the recorded responses.

Once received by the wireless interface 680, the responses recorded by the VEMP sensing arrangement 638 may be analyzed by the processor 682 in, for example, a similar manner as described above with reference to FIGS. 3A-3C and/or FIGS. 4A-4C. For example, the processor 682 may be configured to determine parameters of the electrical stimulation signals delivered to the recipient via the vestibular nerve stimulation arrangement 636 based on an analysis of muscle responses potentially indicative of the vestibular evoked myogenic potentials. The determined stimulation parameters may then be wirelessly transferred to the vestibular nerve stimulator 632 for instantiation (e.g., by processor 642). The determined stimulation parameters may be wirelessly transferred to the vestibular nerve stimulator 632 via the RF link between coils 678 and 641) or another wireless communication channel (not shown in FIG. 6) between wireless interfaces 680 and 670. In this way, the vestibular stimulation system 625 is configured to execute/implement a feedback loop based on an analysis of vestibular evoked myogenic potentials that are evoked by a stimulation of the otolith organs.

FIG. 6 again illustrates an example arrangement in which one VEMP sensing arrangement 638 is used to capture responses associated with vestibular evoked myogenic potentials. However, it is to be appreciated that, in an alternative embodiment, two VEMP sensing arrangements 638 may be provided. In such arrangements, a first one of the VEMP sensing arrangements 638 is configured to record sternocleidomastoid muscle responses associated the cervical vestibular evoked myogenic potential, while a second one of the VEMP sensing arrangements 638 is configured to record the extra ocular muscle responses associated with the ocular vestibular evoked myogenic potential. Both of the VEMP sensing arrangements 638 would provide their associated recorded responses to the vestibular nerve stimulator 632 via wireless interface 670 for subsequent analysis by the processor 682. In such an example, the processor 682 may be configured to execute the analysis of FIGS. 3A-3C and that of FIGS. 4A-4C to, for example, set the stimulation parameters, as described above.

FIGS. 5 and 6 illustrate two additional arrangements, beyond the arrangement shown in FIGS. 2A and 2B, for a vestibular stimulation system in accordance with embodiments presented herein. As noted above, it is to be appreciated that these vestibular stimulation system arrangements are illustrative and that the techniques presented herein may be implemented in vestibular stimulation systems having different arrangements.

Figure 7:
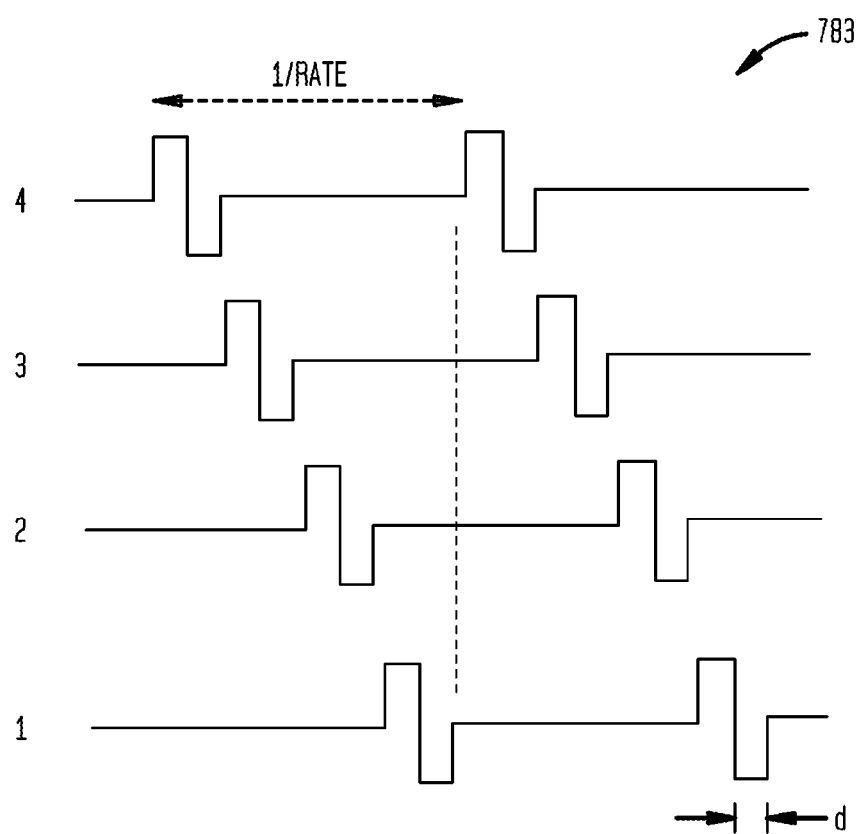
FIG. 7 illustrates portions of electrical stimulation signals that may be delivered to a recipient's vestibular system, in accordance with certain embodiments presented herein.

FIG. 7 illustrates portions of example electrical stimulation signals 783 (trains of current pulses) that may be delivered to a recipient's vestibular system, in accordance with certain embodiments presented herein. In the example of FIG. 7, the pulse rate is 900 Hertz (Hz) (i.e., 1/rate equals 900 pulses per second) and the pulse gap (d) is 25 microseconds. The dynamic range may be between 1 current level (CL) and 170 CL, for example. These specific stimulation parameters are merely illustrative and, as noted, embodiments presented herein use vestibular evoked myogenic potentials to set/adjust the parameters (e.g., stimulation rate, current level, etc.) of the electrical stimulation signals 783.

FIG. 8 is a flowchart of a method 890 in accordance with embodiments presented herein. Method 890 begins at 892 where one or more stimulation electrodes configured to be implanted in the recipient are used to deliver electrical stimulation signals to a vestibular system of a recipient. At 894, following delivery of the electrical stimulation signals, one or more sense electrodes configured to be implanted in the recipient are used to record muscle responses potentially representative of one or more vestibular evoked myogenic potentials. At 896, one or more processors analyze the muscle responses potentially representative of one or more vestibular evoked myogenic potentials. At 896, the one or more processors set one or more parameters of the electrical stimulation signals based on the analysis of the muscle responses.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The invention claimed is:

1. A method, comprising:
 delivering, via one or more stimulation electrodes in a recipient, electrical stimulation signals to a vestibular system of a recipient;
 following delivery of the electrical stimulation signals, recording, via one or more sense electrodes in a recipient, muscle responses, wherein the muscle responses comprise sternocleidomastoid muscle responses;
 comparing the muscle responses to one or more target vestibular evoked myogenic potentials, wherein the one or more target vestibular evoked myogenic potentials comprise one or more target cervical vestibular evoked myogenic potentials (cVEMPs); and
 setting one or more parameters of the electrical stimulation signals based on the comparing of the muscle responses to the one or more target vestibular evoked myogenic potentials.

2. The method of claim 1, wherein delivering the electrical stimulation signals to the vestibular system of the recipient comprises:
 delivering the electrical stimulation signals to at least one of a saccule or an inferior nerve branch of the vestibular system.

3. The method of claim 1, wherein delivering the electrical stimulation signals to the vestibular system of the recipient comprises:
 delivering the electrical stimulation signals to at least one of an utricle or a superior nerve branch of the vestibular system.

4. The method of claim 1, wherein the muscle responses further comprise extra ocular muscle responses, and the one or more target vestibular evoked myogenic potentials comprise one or more target ocular vestibular evoked myogenic potentials (oVEMPs).

5. The method of claim 1, wherein comparing the muscle responses to the one or more target vestibular evoked myogenic potentials comprises:
 determining voltages recorded in muscle of the recipient over the period of time; and
 comparing attributes of the voltages recorded in the muscle of the recipient to the one or more target vestibular evoked myogenic potentials over the period of time.

6. The method of claim 5, wherein the attributes of the voltages recorded in the muscle of the recipient over the period of time comprise:
 with respect to a time of delivery of the electrical stimulation signals, a first time of occurrence for a positive voltage peak associated with the muscle responses; and
 with respect to the time of delivery of the electrical stimulation signals, a second time of occurrence of a negative voltage peak associated with the muscle responses.

7. The method of claim 1, wherein setting the one or more parameters of the electrical stimulation signals based on the comparing of the muscle responses to the one or more target vestibular evoked myogenic potentials comprises:
 reducing an amplitude of the electrical stimulation signals based on the comparing of the muscle responses to the one or more target vestibular evoked myogenic potentials.

8. The method of claim 1, wherein setting the one or more parameters of the electrical stimulation signals based on the comparing of the muscle responses to the one or more target vestibular evoked myogenic potentials comprises:
 setting one or more of a frequency, a pulse rate, or a pulse gap of the electrical stimulation signals based on the comparing of the muscle responses to the one or more target vestibular evoked myogenic potentials.

9. A vestibular stimulation system, comprising:
 a stimulating assembly comprising a plurality of electrodes configured to be implanted in an inner ear of a recipient adjacent to otolith organs of the inner ear;
 a stimulator unit configured to generate and deliver electrical stimulation signals to at least one of the otolith organs via one or more of the plurality of electrodes;
 a vestibular evoked myogenic potential sensing arrangement configured to record, over a period of time following delivery of the electrical stimulation signals to the at least one of the otolith organs, responses from one or more muscles of the recipient; and
 one or more processors configured to set at least one parameter of the electrical stimulation signals based on the responses recorded from the one or more muscles of the recipient in comparison with target vestibular evoked myogenic potentials over the period of time by:
  comparing, with respect to a time of delivery of the electrical stimulation signals, a first time of occurrence for a positive voltage peak associated with the responses to a first threshold time associated with the target vestibular evoked myogenic potentials; and
  comparing, with respect to the time of delivery of the electrical stimulation signals, a second time of occurrence for a negative voltage peak associated with the responses to a second threshold time associated with the target vestibular evoked myogenic potentials.

10. The vestibular stimulation system of claim 9, wherein the vestibular evoked myogenic potential sensing arrangement comprises at least first and second additional electrodes configured to be positioned adjacent a sternocleidomastoid muscle of the recipient.

11. The vestibular stimulation system of claim 9, wherein the vestibular evoked myogenic potential sensing arrangement comprises at least first and second additional electrodes configured to be positioned adjacent an extra ocular muscle of the recipient.

12. The vestibular stimulation system of claim 9, wherein the vestibular evoked myogenic potential sensing arrangement comprises a first set of at least two additional electrodes configured to be positioned adjacent a sternocleidomastoid muscle of the recipient, and wherein the vestibular stimulation system further includes:
 a second vestibular evoked myogenic potential sensing arrangement comprising a second set of at least two other electrodes configured to be positioned adjacent an extra ocular muscle of the recipient.

13. The vestibular stimulation system of claim 9, wherein to set the at least one parameter of the electrical stimulation signals based on the responses recorded from the one or more muscles of the recipient in comparison with the target vestibular evoked myogenic potentials, the one or more processors are configured to:
 determine whether the responses recorded from the one or more muscles of the recipient include at least one vestibular evoked myogenic potential based on the responses recorded from the one or more muscles of the recipient in comparison with the target vestibular evoked myogenic potentials.

14. The vestibular stimulation system of claim 9, wherein to set the at least one parameter of the electrical stimulation signals based on the responses recorded from the one or more muscles of the recipient in comparison with the target vestibular evoked myogenic potentials, the one or more processors are configured to:
 set an amplitude of the electrical stimulation signals based on the responses recorded from the one or more muscles of the recipient in comparison with the target vestibular evoked myogenic potentials.

15. The vestibular stimulation system of claim 9, wherein to set the at least one parameter of the electrical stimulation signals based on the responses recorded from the one or more muscles of the recipient in comparison with the target vestibular evoked myogenic potentials, the one or more processors are configured to:
 set one or more of a frequency, a pulse rate, or a pulse gap of the electrical stimulation signals based on the responses recorded from the one or more muscles of the recipient in comparison with the target vestibular evoked myogenic potentials.

16. The vestibular stimulation system of claim 9, wherein the one or more processors are configured to set the at least one parameter of the electrical stimulation signals based on the responses recorded from the one or more muscles of the recipient in comparison with the target vestibular evoked myogenic potentials over the period of time by reducing an amplitude of the electrical stimulation signals in response to determining the first time of occurrence with respect to the time of delivery of the electrical stimulation signals for the positive voltage peak does not match the first threshold time, determining the second time of occurrence with respect to the time of delivery of the electrical stimulation signals for the negative voltage peak does not match the second threshold time, or both.

17. A method, comprising:
 delivering, via one or more stimulation electrodes in a recipient, electrical stimulation signals to a vestibular system of a recipient;
 following delivery of the electrical stimulation signals, recording, via one or more sense electrodes in a recipient, muscle responses, wherein the muscle responses comprise extra ocular muscle responses;
 comparing the muscle responses to one or more target vestibular evoked myogenic potentials, wherein the one or more target vestibular evoked myogenic potentials comprise one or more target ocular vestibular evoked myogenic potentials (oVEMPs); and
 setting one or more parameters of the electrical stimulation signals based on the comparing of the muscle responses to the one or more target vestibular evoked myogenic potentials.

18. The method of claim 17, wherein comparing the muscle responses to the one or more target vestibular evoked myogenic potentials comprises:
 determining voltages recorded in the muscle of the recipient over the period of time; and
 comparing attributes of the voltages recorded in the muscle of the recipient to the one or more target vestibular evoked myogenic potentials over the period of time.

19. The method of claim 18, wherein the attributes of the voltages recorded in the muscle of the recipient over the period of time comprise:
 with respect to a time of delivery of the electrical stimulation signals, a first time of occurrence for a positive voltage peak associated with the muscle responses; and
 with respect to the time of delivery of the electrical stimulation signals, a second time of occurrence for a negative voltage peak associated with the muscle responses.

20. A method, comprising:
 delivering, via one or more stimulation electrodes in a recipient, electrical stimulation signals to a vestibular system of a recipient;
 following delivery of the electrical stimulation signals, recording, via one or more sense electrodes in a recipient, muscle responses;
 comparing the muscle responses to one or more target vestibular evoked myogenic potentials by determining voltages recorded in a muscle of the recipient over a period of time and comparing attributes of the voltages recorded in the muscle of the recipient to the one or more target vestibular evoked myogenic potentials over the period of time, wherein the attributes of the voltages recorded in the muscle of the recipient over the period of time comprise:
 with respect to a time of delivery of the electrical stimulation signals, a first time of occurrence for a positive voltage peak associated with the muscle responses; and
 with respect to the time of delivery of the electrical stimulation signals, a second time of occurrence for a negative voltage peak associated with the muscle responses; and
 setting one or more parameters of the electrical stimulation signals based on the comparing of the muscle responses to the one or more target vestibular evoked myogenic potentials.

21. The method of claim 20, wherein the muscle responses comprise sternocleidomastoid muscle responses, and the one or more target vestibular evoked myogenic potentials comprise one or more target cervical vestibular evoked myogenic potentials (cVEMPs).

22. The method of claim 20, wherein the muscle responses comprise extra ocular muscle responses, and the one or more target vestibular evoked myogenic potentials comprise one or more target ocular vestibular evoked myogenic potentials (oVEMPs).

23. A method, comprising:
delivering, via one or more stimulation electrodes in a recipient, electrical stimulation signals to a vestibular system of a recipient;
following delivery of the electrical stimulation signals, recording, via one or more sense electrodes in a recipient, muscle responses;
comparing the muscle responses to one or more target vestibular evoked myogenic potentials by determining voltages recorded in a muscle of the recipient over a period of time and comparing attributes of the voltages recorded in the muscle of the recipient to the one or more target vestibular evoked myogenic potentials over the period of time, wherein the attributes of the voltages recorded in the muscle of the recipient over the period of time comprise:
  with respect to a time of delivery of the electrical stimulation signals, a first time of occurrence for a positive voltage peak associated with the muscle responses; and
  with respect to the time of delivery of the electrical stimulation signals, a second time of occurrence for a negative voltage peak associated with the muscle responses; and
setting one or more parameters of the electrical stimulation signals based on the comparing of the muscle responses to the one or more target vestibular evoked myogenic potentials by reducing an amplitude of the electrical stimulation signals in response to determining the first time of occurrence with respect to the time of delivery of the electrical stimulation signals for the positive voltage peak does not match a first threshold time, determining the second time of occurrence with respect to the time of delivery of the electrical stimulation signals for the negative voltage peak does not match a second threshold time, or both.

* * * * *